United States Patent
Song et al.

(10) Patent No.: US 9,447,054 B2
(45) Date of Patent: Sep. 20, 2016

(54) ANTICANCER SUPPLEMENT AGENT INCLUDING BENZO[D]OXAZOL DERIVATIVE AS EFFECTIVE INGREDIENT

(71) Applicant: KOREA INSTITUTE OF RADIOLOGICAL & MEDICAL SCIENCES, Seoul (KR)

(72) Inventors: Jie Young Song, Goyang-si (KR); Ji Yeon Ahn, Seoul (KR); In Sung Jung, Seoul (KR); Saelooom Lee, Seoul (KR); Arang Son, Seoul (KR); Ky Youb Nam, Goyang-si (KR); Hyun Kyung Choi, Suwon-si (KR); Seung Yong Seo, Incheon (KR); Yuan Yue, Incheon (KR)

(73) Assignee: KOREA INSTITUTE OF RADIOLOGICAL & MEDICAL SCIENCES, Seoul (KR)

( * ) Notice: Subject to any disclaimer, the term of this patent is extended or adjusted under 35 U.S.C. 154(b) by 0 days.

(21) Appl. No.: 14/591,885

(22) Filed: Jan. 7, 2015

(65) Prior Publication Data

US 2015/0197498 A1   Jul. 16, 2015

(30) Foreign Application Priority Data

Jan. 15, 2014 (KR) .................. 10-2014-0005150
Dec. 30, 2014 (KR) .................. 10-2014-0193138

(51) Int. Cl.
*C07D 263/57* (2006.01)
*A61K 31/423* (2006.01)

(52) U.S. Cl.
CPC ........... *C07D 263/57* (2013.01); *A61K 31/423* (2013.01)

(58) Field of Classification Search
CPC   C07D 261/20; C07D 413/12; C07D 413/14; C07D 231/14; C07D 263/60
USPC ....................................... 548/241
See application file for complete search history.

(56) References Cited

FOREIGN PATENT DOCUMENTS

| CN | 102617478 A | * | 8/2012 | |
|---|---|---|---|---|
| KR | 10-2007-0096241 | | 10/2007 | |
| WO | WO 2007101224 A2 | * | 9/2007 | ............. A61K 31/00 |

* cited by examiner

*Primary Examiner* — Alicia L Otton
*Assistant Examiner* — Sagar Patel
(74) *Attorney, Agent, or Firm* — Revolution IP, PLLC

(57) ABSTRACT

Disclosed is an anticancer supplement agent including a benzo[d]oxazole derivative as an effective ingredient. The benzo[d]oxazole derivative, which is a nuclear factor E2-related factor 2 (Nrf2) inhibitor, is capable of inhibiting activity of Nrf2 that induces an antioxidant enzyme to remove reactive oxygen species (ROS) that kills a cancer cell, thereby increasing production of ROS. Therefore, the benzo[d]oxazole derivative can be used as an anticancer supplement agent that shows therapeutic effects in anticancer agent therapy or radiation therapy, and in this regard, the benzo[d]oxazole derivative can overcome tolerance of the cancer cell to anticancer agent therapy or radiation therapy and enhance apoptotic effects on the cancer cell.

10 Claims, 8 Drawing Sheets

ANTICANCER SUPPLEMENT AGENT INCLUDING BENZO[D]OXAZOL DERIVATIVE AS EFFECTIVE INGREDIENT

RELATED APPLICATION

This application claims the benefit of Korean Patent Application No. 10-2014-0005150 filed on Jan. 15, 2014 and Korean Patent Application No. 10-2014-0193138 filed on Dec. 30, 2014 in the Korean Intellectual Property Office, the disclosure of which is incorporated herein in its entirety by reference.

BACKGROUND

1. Field

The present disclosure relates to an anticancer supplement agent that can be used in combination during anticancer therapy or radiation therapy, to enhance apoptotic effects on a cancer cell during therapy.

2. Description of the Related Art

In consideration of cancer treatment, surgery, radiation therapy, anticancer therapy, and the like have been widely used, and if necessary, such therapy may be used in combination. About 35% of patients with cancer in Korea and about 50% of patients with cancer in U.S.A have been receiving radiation therapy. According to a trend increasing a number of patients who receive radiation therapy every year, importance of radiation therapy is also more considered. In the case of cancer therapy by surgery, such a surgical treatment may be used in combination with radiation therapy and anticancer therapy, so that recurrence of cancer or metastasis may be inhibited. In this regard, use of high-dose radiation therapy or anticancer agents with high dosage is required, but in reality, dose or dosage of the radiation or the anticancer agent, respectively, is limitedly used in consideration of side effects, such as inflammation or necrosis of a topical region, damage on a normal tissue, or toxicity of an anticancer agent upon systematic drug administration. In addition, as a method of solving problems with resistance or tolerance to anticancer therapy or radiation therapy and minimizing a damage of a normal tissue to enhance cancer therapeutic effects, use of an enhancer or a supplement agent for anticancer therapy and radiation therapy is now more considered.

Cancer cells secrete more antioxidant enzymes, which are capable of removing reactive oxygen species (ROS), than normal cells, and accordingly, cancer cells have a tolerance to radiation of radiation therapy and an anticancer agent of anticancer therapy. In most cases, expression of an antioxidant enzyme is controlled by a transcription factor, nuclear factor E2-related factor 2 (Nrf2). Under normal conditions without oxidative stress, Nrf2 binds to Kelch-like ECH-associated protein 1 (Keap1) in the cytoplasm, resulting in proteasomal degradation. Under oxidative stress such as exposure to radiation, Nrf2 separated from Keap1 translocates into the nucleus and binds to an antioxidant response element (ARE) present within a promoter of an antioxidant enzyme gene, resulting in the expression of various antioxidant enzymes to remove oxidative stress. However, in cancer cells, especially cells of lung cancer and prostate cancer, without oxidant stress, mutations of the Nrf2 gene may occur, resulting in continuous expression of the Nrf2 gene. Alternatively, mutations of a Keap1 gene that is antagonistic to the Nrf2 gene may occur, resulting in loss of the Keap1 gene function, and in this regard, Nrf2 may move into a nucleus for over-expression of the antioxidant enzyme.

In addition, in the case of radiation therapy, activity of Nrf2 can be further enhanced to remove ROS.

Increase in the number of electrophiles of an anticancer agent or in activity of the Nrf2 transcription factor according to ROX signals of the radiation may interfere with cancer therapeutic effects by anticancer therapy and radiation therapy. In particular, the Nrf2 transcription factor in cells of lung cancer is consistently activated, so that cancer treatment is known to be very difficult.

Doxorubicin (as known as adriamycin) as a topoisomerase II inhibitor causes generation of ROS and is an anticancer agent having an action mechanism of damaging the DNA of cancer cells. Doxorubicin is significantly effective in the treatment of not only solid cancer, e.g., lung cancer and colorectal cancer, but also blood cancer, e.g., leukemia. However, cancer cells with the increased activity of the Nrf2 transcription factor may induce the expression of the antioxidant enzyme, e.g., heme oxygenase-1 (HO-1) that can offset the action mechanism of doxorubicin by the Nrf2 transcription factor, resulting in doxorubicin-resistant cancer cells. In this regard, if the activity of Nrf2 is inhibited in an efficient manner, the resistance of the cancer cell to doxorubicin may be reduced, thereby enhancing anticancer effects.

As described above, the activation of Nrf2 is considered as a main cause of cancer cell's resistance to anticancer agent therapy or radiation therapy. Therefore, research about identifying a Nrf2 inhibitor and about developing a combined treatment for the enhancement of apoptosis of the cancer cells through chemotherapy or radiation therapy in combination with the cancer cells is demanded.

RELATED ART

Patent Document

KR 2007-0096241

SUMMARY

Provided is a composition including a benzo[d]oxazole derivative as an anticancer supplement agent, wherein the benzo[d]oxazole is a Nrf2 inhibitor that inhibits activity of Nrf2 in a cancer cell to overcome tolerance to an anticancer agent or radiation and to enhance effects on apoptosis of the cancer cell in consideration of anticancer agent therapy or radiation therapy. The composition including the anticancer supplement agent can be used in combination during anticancer agent therapy or radiation therapy. In this regard, administration of the composition in combination may result in overcome tolerance to anticancer agent therapy or radiation therapy and enhanced effects of anticancer activity with respect to a cancer cell.

Additional aspects will be set forth in part in the description which follows and, in part, will be apparent from the description, or may be learned by practice of the presented exemplary embodiments According to an aspect of an exemplary embodiment, an anticancer supplement agent includes a benzo[d]oxazole derivative as an effective ingredient that is represented by Formula 1 below.

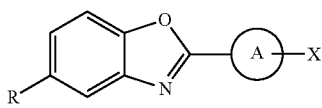

[Formula 1]

In Formula 1, R may be selected from the group consisting of —NH₂ and —OH, A may be selected from the group consisting of a benzene, naphthyl, and anthracenyl, X may be selected from the group consisting of a halogen, a hydrogen, a $C_1$-$C_4$ alkyl group, a $C_1$-$C_4$ alkoxy group, a phenyl group, and a phenyl group substituted with at least one of methoxy, trifluoromethyl, and a halogen.

In the benzo[d]oxazole derivative, A may be selected from the group consisting of benzene and naphthyl, X may be selected from the group consisting of a hydrogen, a $C_1$-$C_4$ alkyl group, a phenyl group, and a phenyl group substituted with at least one of a methoxy, a trifluoromethyl, and a halogen.

The benzo[d]oxazole derivative may be at least one selected from the group consisting of 2-(5-bromonaphtha-lene-1-yl)benzo[d]oxazole-5-amine, 2-(naphthalene-1-yl)benzo[d]oxazole-5-amine, 2-(naphthalene-2-yl)-benzo[d]oxazole-5-amine, 2-(4-tert-butylphenyl)benzo[d]oxazole-5-amine, 2-(5-chloronaphthalene-1-yl)benzo[d]oxazole-5-amine, 2-([1,1'-biphenyl]-4-yl)benzo[d]oxazole-5-amine, 2-(3',4',5'-trimethoxy-[1,1'-biphenyl]-4-yl)benzo[d]oxazole-5-amine, 2-(4'-trifluoromethyl-[1,1'-biphenyl]-4-yl)benzo[d]oxazole-5-amine, 2-(4'-chloro-[1,1'-biphenyl]-4-yl)benzo[d]oxazole-6-ol and 2-(2'-methoxy-[1,1'-biphenyl]-4-yl)benzo[d]oxazole-6-ol.

According to an aspect of an exemplary embodiment, there is provided a pharmaceutical composition for preventing or treating cancer, wherein the pharmaceutical composition includes an anticancer agent and a benzo[d]oxazole derivative as an effective ingredient that is represented by Formula 1 above.

According to another aspect of an exemplary embodiment, there is provided a radiosensitive enhancer, wherein the enhancer includes a benzo[d]oxazole derivative as an effective ingredient that is represented by Formula 1 above.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
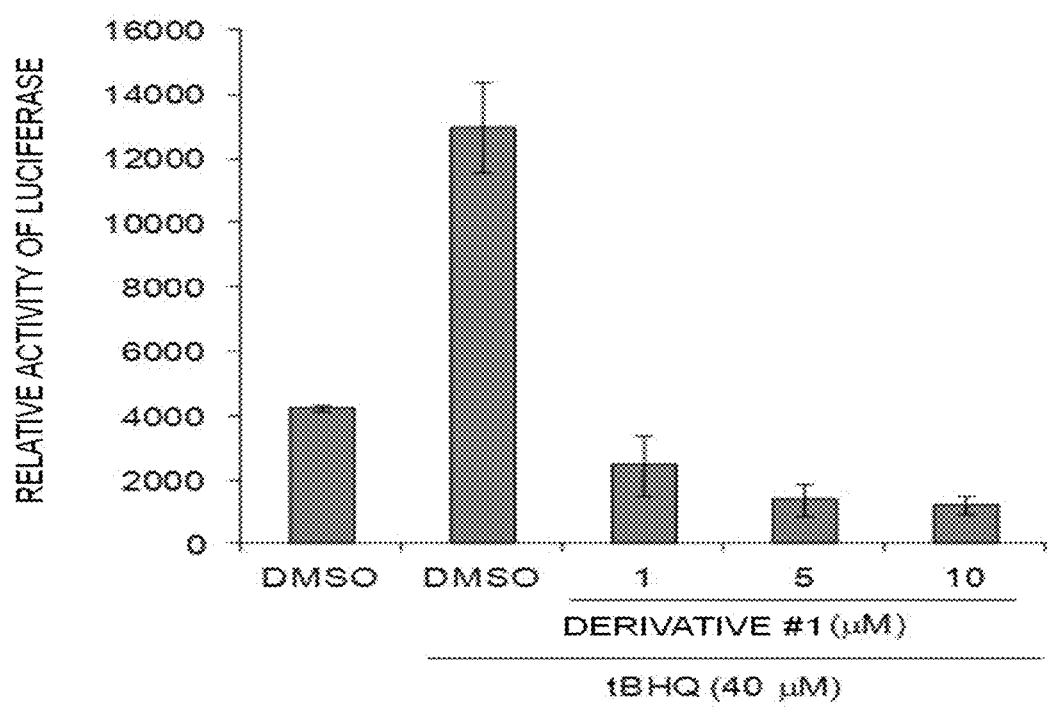
FIG. 1 shows a result of inhibitory effects of concentration-dependent Nrf2-responsive luciferase in a case where Nrf2-responsive luciferase whose activity is increased by tert-butylhydroquinone (tBHQ) of lung cancer cell strain (H1299) is treated with 2-(5-bromonaphthalene-1-yl)benzo[d]oxazole-5-amine (Derivative #1) in a concentration of 1 μM, 5 μM, and 10 μM.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects. Expressions such as "at least one of," when preceding a list of elements, modify the entire list of elements and do not modify the individual elements of the list.

According to an exemplary embodiment, there is provided an anticancer supplement agent including a benzo[d]oxazole derivate as an effective ingredient that is represented by Formula 1 below.

[Formula 1]

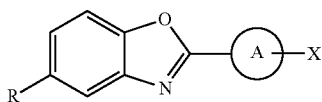

In Formula 1, R may be selected from the group consisting of —$NH_2$ and —OH, A may be selected from the group consisting of benzene, naphthyl, and anthracenyl, and X may be selected from the group consisting of halogen, hydrogen, a $C_1$-$C_4$ alkyl group, a $C_1$-$C_4$ alkoxy group, phenyl and phenyl substituted with at least one of methoxy, trifluoromethyl, and halogen.

In the benzo[d]oxazole derivate, A may be selected from the group consisting of benzene and naphthyl, and X may be selected from the group consisting of halogen, hydrogen, a $C_1$-$C_4$ alkyl group, phenyl, and phenyl substituted with at least one of methoxy, trifluoromethyl, and halogen.

The benzo[d]oxazole derivate may be at least one selected from the group consisting of 2-(5-bromonaphthalene-1-yl)benzo[d]oxazole-5-amine, 2-(naphthalene-1-yl)benzo[d]oxazole-5-amine, 2-(naphthalene-2-yl)-benzo[d]oxazole-5-amine, 2-(4-tert-butylphenyl)benzo[d]oxazole-5-amine, 2-(5-chloronaphthalene-1-yl)benzo[d]oxazole-5-amine, 2-([1,1'-biphenyl]-4-yl)benzo[d]oxazole-5-amine, 2-(3',4',6-trimethoxy-[1,1'-biphenyl]-4-yl)benzo[d]oxazole-5-amine, 2-(4'-trifluoromethyl-[1,1'-biphenyl]-4-yl)benzo[d]oxazole-5-amine, 2-(4'-chloro-[1,1'-biphenyl]-4-yl)benzo[d]oxazole-6-ol, and 2-(2'-methoxy-[1,1'-biphenyl]-4-yl)benzo[d]oxazole-6-ol, which are represented by Formulae 2 to 11 below:

[Formula 2]

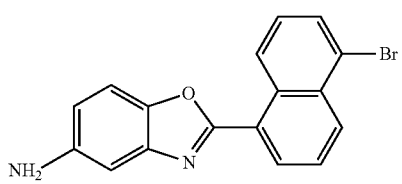

2-(5-bromonaphthalene-1-yl)benzo[d]oxazole-5-amine (Derivative #1)

[Formula 3]

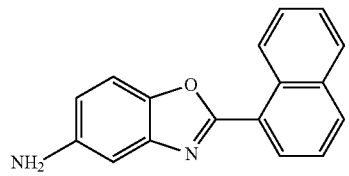

2-(naphthalene-1-yl)benzo[d]oxazole-5-amine (Derivative #2)

[Formula 4]

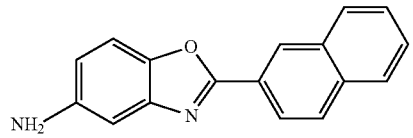

2-(naphthalene-2-yl)benzo[d]oxazole-5-amine (Derivative #3)

[Formula 5]

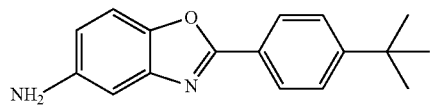

2-(4-tert-butylphenyl)benzo[d]oxazole-5-amine (Derivative #4)

[Formula 6]

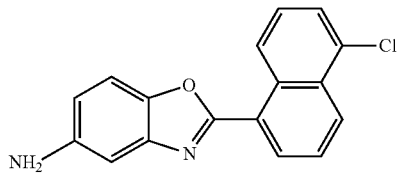

2-(5-chloronahthalene-1-yl)benzo[d]oxazole-5-amine (Derivative #5)

[Formula 7]

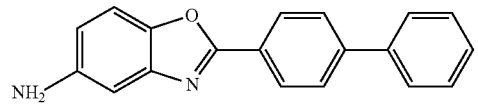

2-([1,1'-biphenyl]-4-yl)benzo[d]oxazole-5-amine (Derivative #6)

[Formula 8]

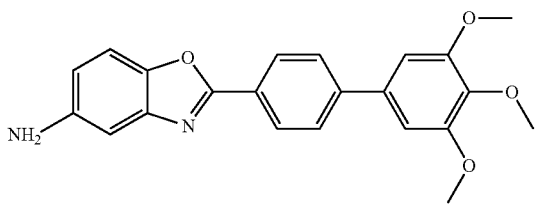

2-(3',4',5'-trimethoxy-[1,1'-biphenyl]-4-yl)benzo[d]oxazole-5-amine (Derivative #7)

[Formula 9]

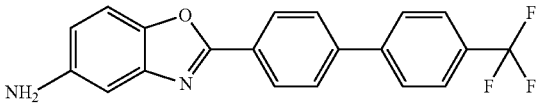

2-(4'-trifluoromethyl-[1,1'-biphenyl]-4-yl)benzo[d]oxazole-5-amine (Derivative #8)

-continued

[Formula 10]

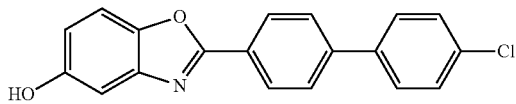

2-(4'-chloro-[1,1'-biphenyl]-4-yl)benzo[d]oxazole-6-ol (Derivative #9)

[Formula 11]

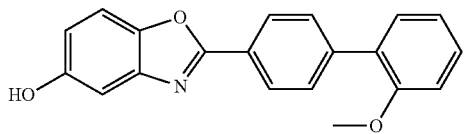

2-(2'-methoxy-[1,1'-biphenyl]-4-yl)benzo[d]oxazole-6-ol (Derivative #10)

The benzo[d]oxazole derivative is capable of increasing apoptosis in cancer cells by inhibiting activity of a nuclear factor E2-related factor 2 (Nrf2) gene.

Figure 5:
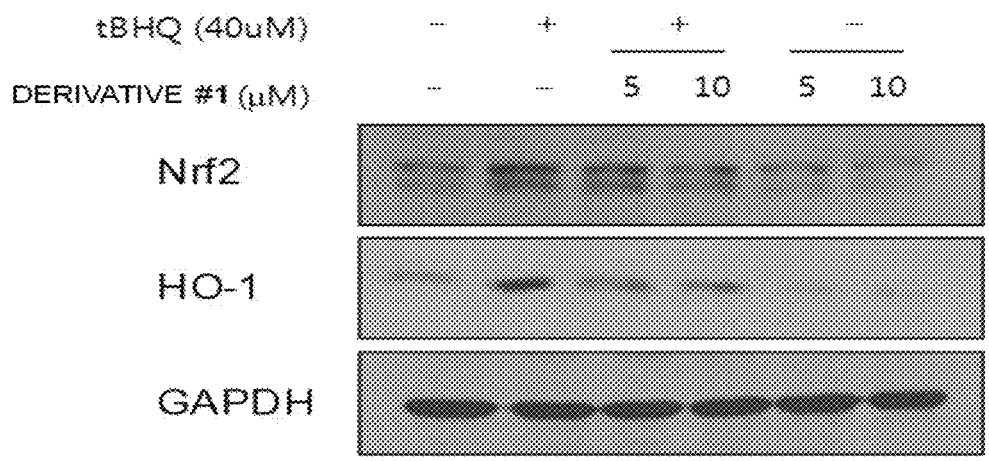
FIG. 5 shows a result of western blotting analysis to confirm inhibition of the expression of Nrf2 protein and HO-1 protein after lung cancer cell is treated with 5 μM or 10 μM of 2-(5-bromonaphthalene-1-yl)benzo[d]oxazole-5-amine (Derivative #1), wherein a GAPDH antibody is used to standardize the amount of analysis.

The benzo[d]oxazole derivative, which serves as a Nrf2 gene inhibitor, may result in, as shown in FIG. 5 showing the results of western blotting analysis in Example 2, reduced amounts of Nrf2 and antioxidant enzyme (e.g., HO-1) proteins that are downstream proteins of Nrf2, in a cell that is treated with a benzo[d]oxazole derivative, e.g., 2-(5-bromonaphthalene-1-yl)benzo[d]oxazole-5-amine (Derivative #1).

Figure 6:
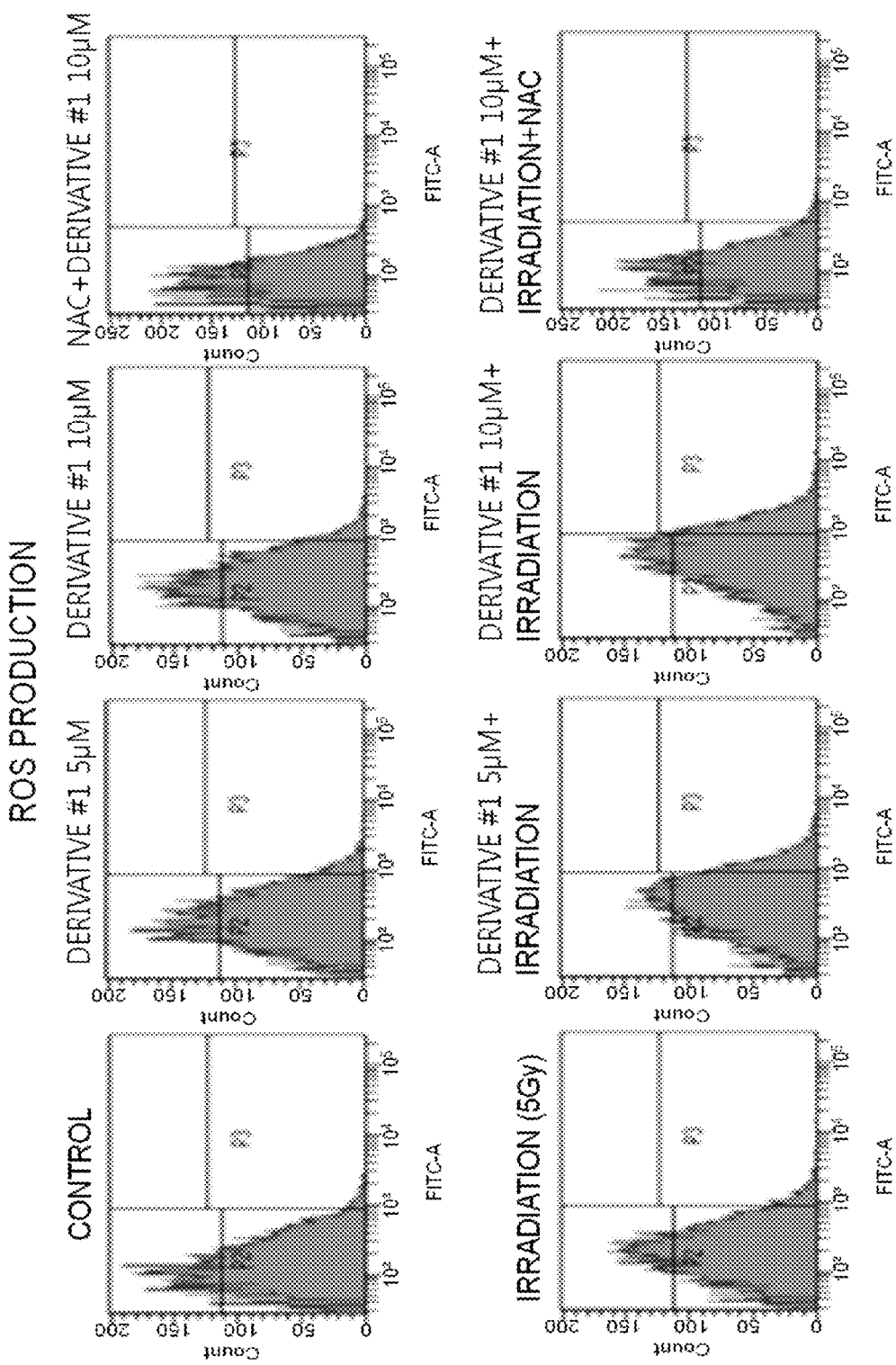
FIG. 6 shows FACS analysis results of measuring amounts of ROS generated in an experimental group where lung cancer cell strain is treated with 5 μM or 10 μM of 2-(5-bromonaphthalene-1-yl)benzo[d]oxazole-5-amine (Derivative #1) as a sensitizer and is treated by irradiation in combination and in a control group where lung cancer cell is treated with Derivative #1 only, wherein FACS analysis is prepared by treating the targets with a ROS inhibitor, e.g., N-acetyl-L-cystein (NAC), to confirm that the measured values refer to the presence of the ROS.
Figure 7:
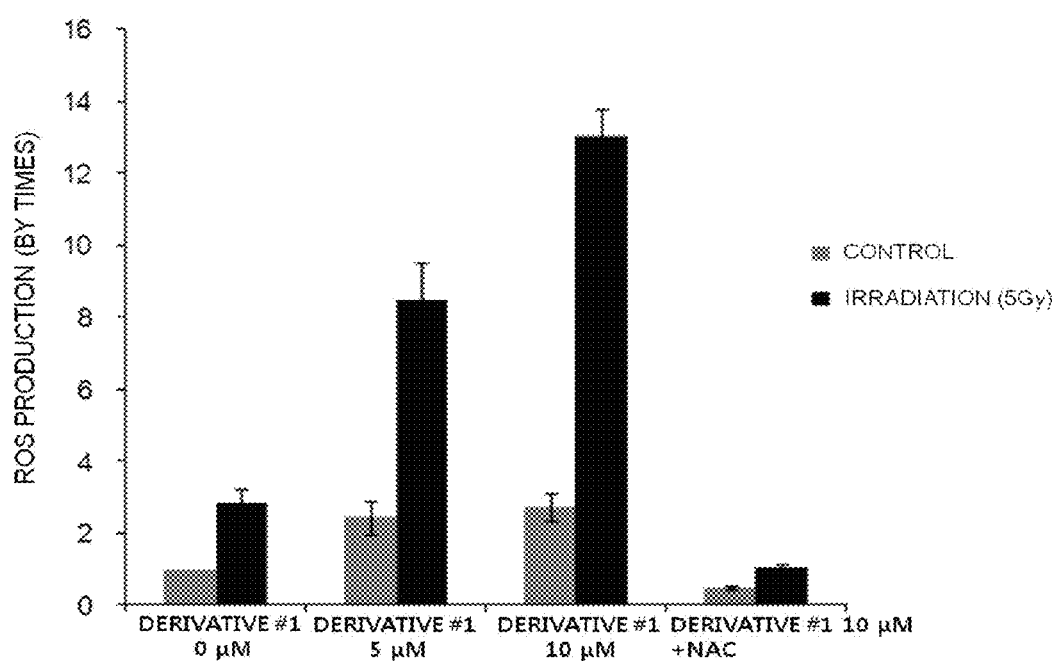
FIG. 7 is a graph of measuring amounts of ROS generated in an experimental group where lung cancer cell strain is treated with 2-(5-bromonaphthalene-1-yl)benzo[d]oxazole-5-amine (Derivative #1) and is treated by irradiation in combination and a control group where lunc carcinoma cell is treated with 2-(5-bromonaphthalene-1-yl)benzo[d]oxazole-5-amine (Derivative #1) only.
Figure 8:
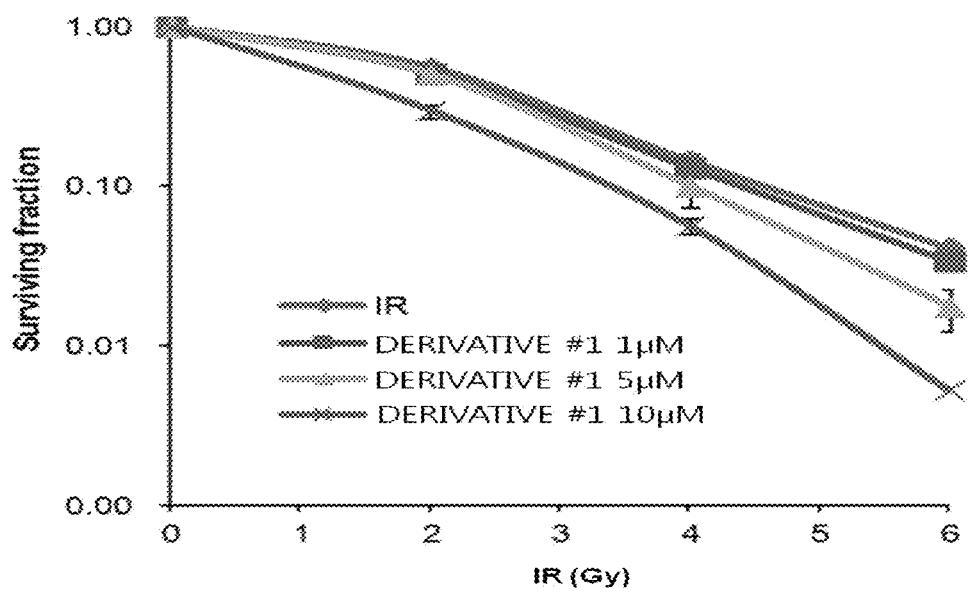
FIG. 8 shows a result of enhanced radiation sensitivity effects of lung cancer cells measured by using a chlorogenic method after cells of the lung cancer cell strain (H1299) are treated with 2-(5-bromonaphthalene-1-yl)benzo[d]oxazole-5-amine (Derivative #1) in a concentration of 1 μM, 5 μM, and 10 μM and irradiated according to radiation doses.
Figure 9:
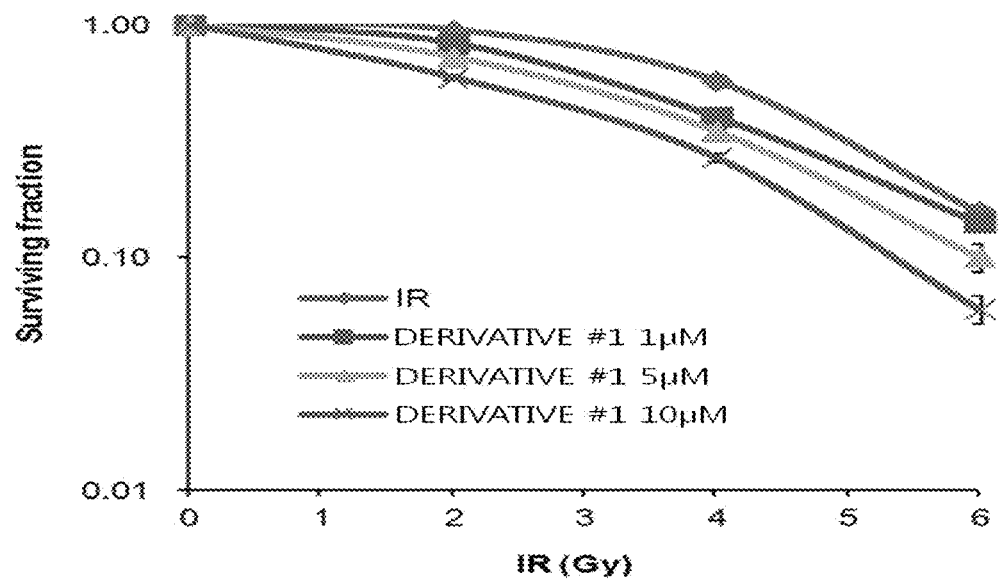
FIG. 9 shows a result of enhanced radiation sensitivity effects of brain tumor cells measured by using a chlorogenic method after cells of the brain tumor cell strain (U87MG) are treated with 2-(5-bromonaphthalene-1-yl)benzo[d]oxazole-5-amine (Derivative #1) in a concentration of 1 μM, 5 μM, and 10 μM and irradiated according to radiation doses.
Figure 10:
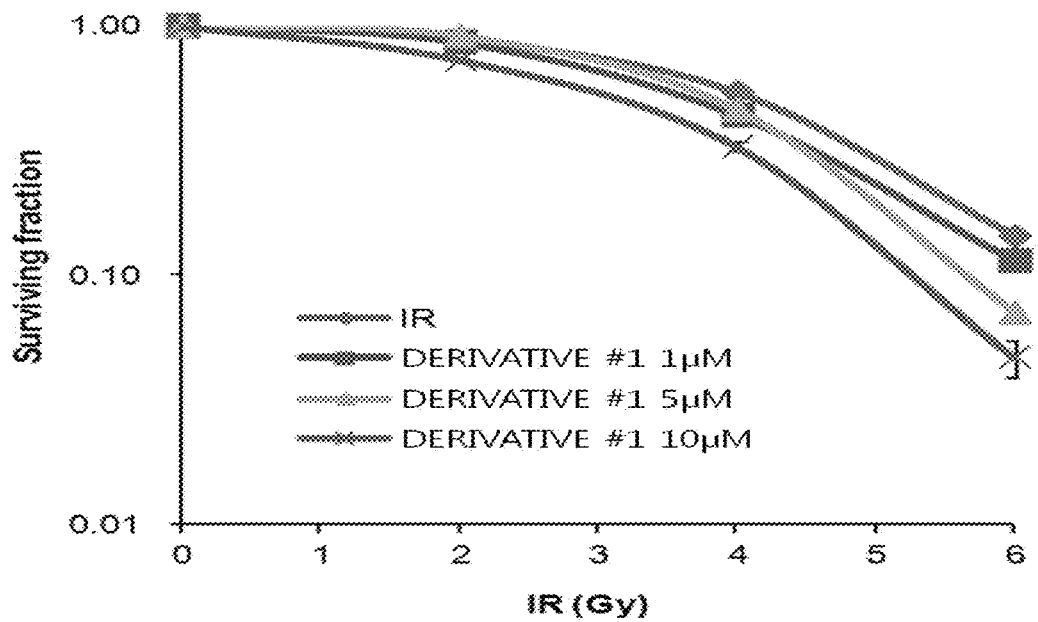
FIG. 10 shows a result of enhanced radiation sensitivity effects of breast cancer cells measured by using a chlorogenic method after cells of the breast cancer cell strain (MDA-MB231) are treated with 2-(5-bromonaphthalene-1-yl)benzo[d]oxazole-5-amine (Derivative #1) in a concentration of 1 μM, 5 μM, and 10 μM and irradiated according to radiation doses.
Figure 11:
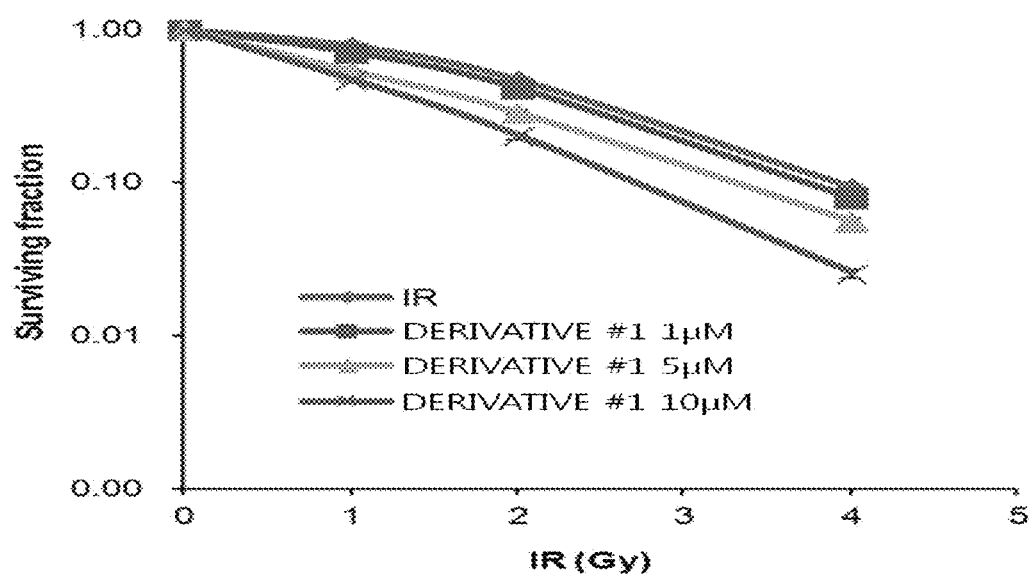
FIG. 11 is shows a result of enhanced radiation sensitivity effects of colorectal cancer cells measured by using a chlorogenic method after the cells of colorectal cancer cell strain (HCT116) are treated with 2-(5-bromonaphthalene-1-yl)benzo[d]oxazole-5-amine (Derivative #1) in a concentration of 1 μM, 5 μM, and 10 μM and irradiated according to radiation doses.

In a case where a lung cancer cell is treated with a benzo[d]oxazole derivative, which serves as a Nrf2 gene inhibitor, and radiation in combination, amounts of reactive oxygen species (ROS) generated herein are measured as shown in FIGS. 6 and 7. Referring to these figures, it is found that the incidence of ROS in experimental groups treated in combination with 2-(5-bromonaphthalene-1-yl) benzo[d]oxazole-5-amine (Derivative #1) and radiation is significantly increased as compared with the incidence of ROS in control groups.

Accordingly, it is confirmed that the benzo[d]oxazole derivative of the present inventive concept serves as a Nrf2 gene inhibitor and has capability of inhibiting gene expression that is regulated by antioxidant response element (ARE) and increasing generation of ROS.

In this regard, the benzo[d]oxazole derivatives may increase anticancer activity of an anticancer agent of radiation on a cancer cell.

According to an exemplary embodiment, cells of lung cancer, brain cancer, breast cancer, and colorectal cancer are treated with 2-(5-bromonaphthalene-1-yl)benzo[d]oxazole-5-amine (Derivative #1) in concentrations of 1 μM to 10 μM, and then, are irradiated. After the cells are stained and a number of the colony-forming cells is counted, as shown in FIGS. 8 to 11, it is found that apoptosis in all cancer cells is increased in an experimental group treated in combination with 2-(5-bromonaphthalene-1-yl)benzo[d]oxazole-5-amine (Derivative #1) and radiation.

In addition, the lung cancer cells are treated with other benzo[d]oxazole derivatives (i.e., Derivative #2 to #10) and radiation in combination, and then, cell viability thereof is measured by using CCK-8. As a result as shown in FIG. 12, it is found that the number of apoptotic cells is increased by 20% in experimental groups treated in combination compared to that in control groups treated with radiation only.

Figure 12:
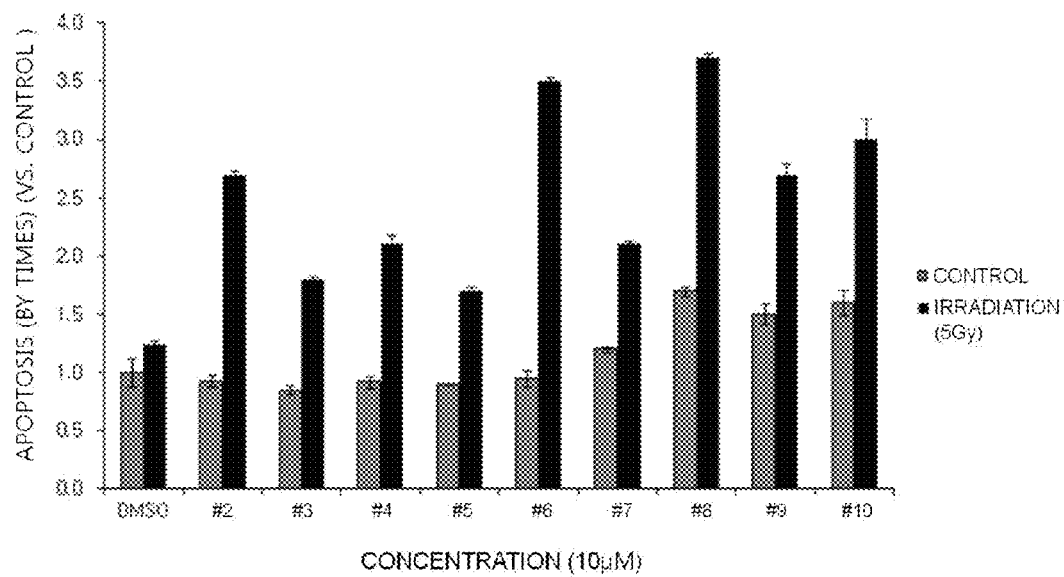
FIG. 12 shows a result of radiation sensitivity based on a number of apoptosis measured by using a CCK-8 analysis kit after cells of lung cancer cell strain (H1299) are treated with 10 μM of each of benzo[d]oxazole derivatives (Derivates 2 to 10) and are treated by radiation (5 Gy) in combination.

According to another exemplary embodiment, when the lung cancer cell strain is treated in combination with the benzo[d]oxazole derivatives and doxorubicin as an anticancer agent, as shown in FIG. 12, the number of apoptotic lung cancer cells that are treated in combination is found to be about 2.1 to 4.5 times as large as the number of apoptotic lung cancer cells that are treated with an anticancer agent only.

The anticancer agent used herein may be selected from the group consisting of a platinum-based anticancer agent, an alkylated anticancer agent, and an anthracycline-based anticancer agent.

Examples of the platinum-based anticancer agent are cisplatin, carboplatin, and oxaliplatin; examples of the alkylate anticancer agent are cyclophosphamide, ifosfamide, melphalan, mechlorethamin, and chlorambucil; examples of the anthracycline-based anticancer agent are doxorubicin, adriamycin, aclarubicin, daunorubicin, and epirubicin, and these examples are not limited thereto.

Another aspect of the present inventive concept provides a pharmaceutical composition for preventing or treating cancer, the pharmaceutical composition including an anticancer agent and a benzo[d]oxazole derivative as an effective ingredient that is represented by Formula 1 below:

[Formula 1]

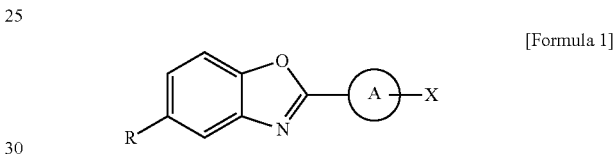

In Formula 1, R may be selected from the group consisting of —$NH_2$ and —OH, A may be selected from the group consisting of benzene, naphthyl, and anthracenyl, and X may be selected from the group consisting of halogen, hydrogen, a $C_1$-$C_4$ alkyl group, a $C_1$-$C_4$ alkoxy group, phenyl, and phenyl substituted with at least one of methoxy, trifluoromethyl, and halogen.

In the benzo[d]oxazole derivative, A may be selected from the group consisting of benzene and naphthyl and X may be selected from the group consisting of halogen, hydrogen, a $C_1$-$C_4$ alkyl group, phenyl, and phenyl substituted with at least one of methoxy, trifluoromethyl, and halogen.

The benzo[d]oxazole derivative may be at least one selected from the group consisting of 2-(5-bromonaphthalene-1-yl)benzo[d]oxazole-5-amine, 2-(naphthalene-1-yl)benzo[d]oxazole-5-amine, 2-(naphthalene-2-yl)-benzo[d]oxazole-5-amine, 2-(4-tert-butylphenyl)benzo[d]oxazole-5-amine, 2-(5-chloronaphthalene-1-yl)benzo[d]oxazole-5-amine, 2-([1,1'-biphenyl]-4-yl)benzo[d]oxazole-5-amine, 2-(3',4',5'-trimethoxy-[1,1'-biphenyl]-4-yl)benzo[d]oxazole-5-amine, 2-(4'-trifluoromethyl-[1,1'-biphenyl]-4-yl)benzo[d]oxazole-5-amine, 2-(4'-chloro-[1,1'-biphenyl]-4-yl)benzo[d]oxazole-6-ol, and 2-(2'-methoxy-[1,1'-biphenyl]-4-yl)benzo[d]oxazole-6-ol that are represented by Formulae 2 to 11.

Examples of the cancer are lung cancer, brain cancer, breast cancer, and colorectal cancer, but are not limited thereto. The anticancer agent may be selected from the group consisting of a platinum-based anticancer agent, an alkylated anticancer, and an anthracycline-based anticancer agent.

The pharmaceutical composition may include an anticancer agent in a range of about 1 to about 99 wt % and a benzo[d]oxazole derivative in a range of about 1 to about 99 wt %, but is not limited thereto.

The pharmaceutical composition according to the present inventive concept may further include a suitable carrier, excipient, or diluent that is commonly used in preparation of a pharmaceutical composition in the art.

Such a carrier, an excipient, or a diluent available in the present inventive concept may be lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, or mineral oil.

The pharmaceutical composition according to the present inventive concept may be formulated as oral formulations, such as powders, granules, tablets, capsules, suspensions, emulsions, syrups, or aerosols, external applications, suppositories, and sterile injectable solutions.

When formulated, a diluent or an excipient, such as fillers, extenders, binders, wetting agents, disintegrating agents, or surfactants, may be used. Examples of solid formulations for oral administration are tablets, pills, powders, granules, and capsules. Such solid formulations are prepared by using at least one excipient, such as starch, calcium carbonate, sucrose or lactose, or gelatin.

In addition to the excipient, a lubricant, such as magnesium stearate and talc may be used for preparation of a solid formulation. As liquid formulations for oral administration, suspensions, oral solutions, emulsions, or syrups may be used. For example, in addition to a commonly used diluents, such as water or liquid paraffin, a various types of an excipient including wetting agents, sweeteners, fragrances, and preservatives may be used for preparation of a solid formulation.

The dosage of the pharmaceutical composition according to the present inventive concept may vary according to a patient's age, gender, weight, or the like. For example, the benzo[d]oxazole derivative may be administered to a patient in a dosage of about 1.0 mg/m$^2$/day to about 1.3 mg/m$^2$/day while the anticancer agent may be administered to a patient in a dosage of about 2 mg/day to about 6 mg/day, twice a week (1 to 4 cycles per administration).

In addition, the dosage of the pharmaceutical composition according to the present inventive concept may vary according to a route of administration, severity of disease, and a patient's gender, weight, age, or the like. In this regard, the dosage of the pharmaceutical composition according to the present inventive concept is not intended to limit the scope of the present inventive concept in any aspect.

The anticancer agent and the benzo[d]oxazole derivative included in the pharmaceutical composition are substances that are already being prescribed for other medical purposes in the art, so that safety of these substances is ensured.

The pharmaceutical composition of the present inventive concept may be administered orally or parenterally according to the method of interest. For example, the pharmaceutical composition may be applied to intravenous, subcutaneous, or intraperitoneal local sites, and the dosage of the pharmaceutical composition may vary according to a patient's weight, age, gender, health condition, diet, administration time, administration method, elimination rates, and severity of the disease In order to prevent or treat cancer, the pharmaceutical composition of the present inventive concept may be used alone, or in combination with surgery, hormone therapy, drug therapy and use of biological response modifiers.

Another aspect of the present inventive concept provides a radiosensitive enhancer including a benzo[d]oxazole derivative as an effective ingredient that is represented by Formula 1 below:

[Formula 1]

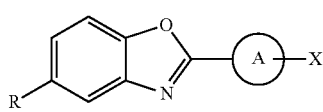

In Formula 1, R may be selected from the group consisting of —NH$_2$ and —OH, A may be selected from the group consisting of benzene, naphthyl, and anthracenyl, and X may be selected from the group consisting of halogen, hydrogen, a C$_1$-C$_4$ alkyl group, a C$_1$-C$_4$ alkoxy group, phenyl and phenyl substituted with at least one of methoxy, trifluoromethyl, and halogen.

In the benzo[d]oxazole derivate, A may be selected from the group consisting of benzene and naphthyl, and X may be selected from the group consisting of halogen, hydrogen, a C$_1$-C$_4$ alkyl group, phenyl, and phenyl substituted with at least one of methoxy, trifluoromethyl, and halogen.

The benzo[d]oxazole derivate may be at least one selected from the group consisting of 2-(5-bromonaphthalene-1-yl)benzo[d]oxazole-5-amine, 2-(naphthalene-1-yl)benzo[d]oxazole-5-amine, 2-(naphthalene-2-yl)-benzo[d]oxazole-5-amine, 2-(4-tert-butylphenyl)benzo[d]oxazole-5-amine, 2-(5-chloronaphthalene-1-yl)benzo[d]oxazole-5-amine, 2-([1,1'-biphenyl]-4-yl)benzo[d]oxazole-5-amine, 2-(3',4',5'-trimethoxy-[1,1'-biphenyl]-4-yl)benzo[d]oxazole-5-amine, 2-(4'-trifluoromethyl-[1,1'-biphenyl]-4-yl)benzo[d]oxazole-5-amine, 2-(4'-chloro-[1,1'-biphenyl]-4-yl)benzo[d]oxazole-6-ol, and 2-(2'-methoxy-[1,1'-biphenyl]-4-yl)benzo[d]oxazole-6-ol.

Hereinafter, examples of the present invention will be described in detail. However, the examples are for illustrative purposes only and are not intended to limit the scope of the present invention.

Synthesis Example 1

Synthesis of
2-(naphthalene-1-yl)benzo[d]oxazole-5-amine
(Derivative #2)

2-(naphthalene-1-yl)benzo[d]oxazole-5-amine (Derivate #2), was synthesized according to Reaction Scheme 1 below:

[Reaction Scheme 1]

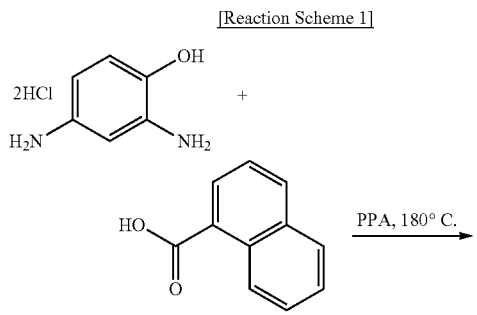

-continued

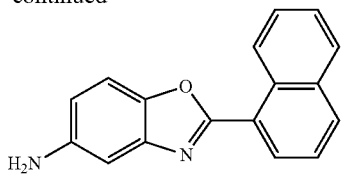

8 mmol of 2,4-diaminophenol.2HCl and 8 mmol of naphthalene-1-carboxylic acid were dissolved in 10 g of polyphosphoric acid (PPA), and then, the mixed solution was stirred at a temperature of 180° C. for 3 to 4 hours. After completion of the reaction, the reaction solution was cooled, neutralized with 10% NaOH, and filtered by using distilled water for recrystallization in a slow manner, thereby obtaining 1.6 g of 2-(naphthalene-1-yl)benzo[d]oxazole-5-amine (Derivative #2) (yield: 77%).

1H NMR (400 MHz, Chloroform-d) δ 8.45-8.35 (m, 1H), 8.05 (t, J=7.5 Hz, 1H), 8.00-7.88 (m, 2H), 7.67 (tt, J=5.0, 2.5 Hz, 1H), 7.53-7.42 (m, 2H), 7.34 (d, J=1.6 Hz, 1H), 7.22 (d, J=7.5 Hz, 1H), 6.85 (dd, J=7.4, 1.5 Hz, 1H), 4.95 (s, 2H).

Synthesis Example 2

Synthesis of 2-(naphthalene-2-yl)benzo[d]oxazole-5-amine (Derivative #3)

2-(naphthalene-2-yl)benzo[d]oxazole-5-amine (Derivative #3) was synthesized according to Reaction Scheme 2 below:

[Reaction Scheme 2]

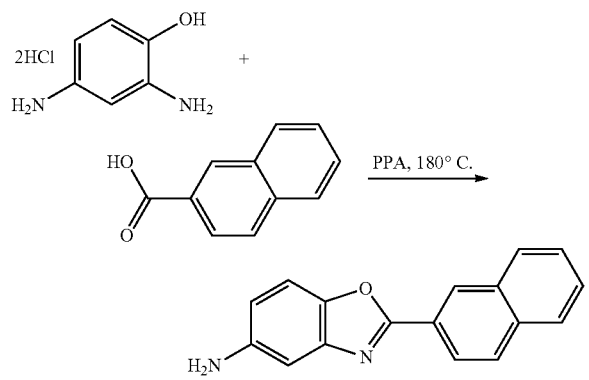

80 μmol of 2,4-diaminophenol.2HCl and 80 μmol of naphthalene-2-carboxylic acid were dissolved in 100 mg of PPA, and then, the mixed solution was stirred at a temperature of 180° C. for 3 to 4 hours. After completion of the reaction, the reaction solution was cooled, neutralized with 10% NaOH, and filtered by using distilled water for recrystallization in a slow manner, thereby obtaining 15.6 mg of 2-(naphthalene-2-yl)benzo[d]oxazole-5-amine (Derivative #3) (yield: 75%).

1H NMR (400 MHz, Chloroform-d) δ 8.53 (d, J=1.5 Hz, 1H), 8.17 (dt, J=7.5, 1.8 Hz, 1H), 8.09 (dd, J=7.5, 1.4 Hz, 1H), 8.01-7.92 (m, 2H), 7.52 (dtd, J=21.4, 7.4, 1.7 Hz, 2H), 7.29 (d, J=1.6 Hz, 1H), 7.21 (d, J=7.6 Hz, 1H), 6.84 (dd, J=7.5, 1.5 Hz, 1H), 3.38 (s, 2H).

Synthesis Example 3

2-(4-tert-butylphenyl)benzo[d]oxazole-5-amine (Derivative #4)

2-(4-tert-butylphenyl)benzo[d]oxazole-5-amine (Derivative #4) was synthesized according to Reaction Scheme 3 below:

[Reaction Scheme 3]

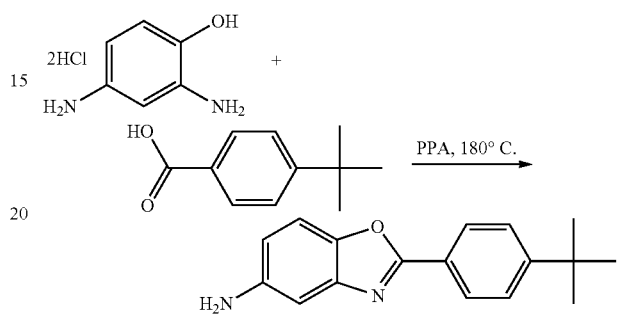

8 mmol of 2,4-diaminophenol.2HCl and 8 mmol of 4-tert-butyl-benzoic acid were dissolved in 10 g of PPA, and then, the mixed solution was stirred at a temperature of 180° C. for 3 to 4 hours. After completion of the reaction, the reaction solution was cooled, neutralized with 10% NaOH, and filtered by using distilled water for recrystallization in a slow manner, thereby obtaining 2.0 g of 2-(4-tert-butylphenyl)benzo[d]oxazole-5-amine (Derivate #4) (yield: 94%).

1H NMR (400 MHz, Chloroform-d) δ 7.71-7.63 (m, 1H), 7.62-7.54 (m, 1H), 7.27-7.16 (m, 1H), 4.08 (s, 1H), 1.28 (s, 5H).

Synthesis Example 4

Synthesis of 2-(5-chloronaphthalene-1-yl)benzo[d]oxazole-5-amine (Derivative #5)

2-(5-chloronaphthalene-1-yl)benzo[d]oxazole-5-amine (Derivative #5) was synthesized according to Reaction Scheme 4 below:

[Reaction Scheme 4]

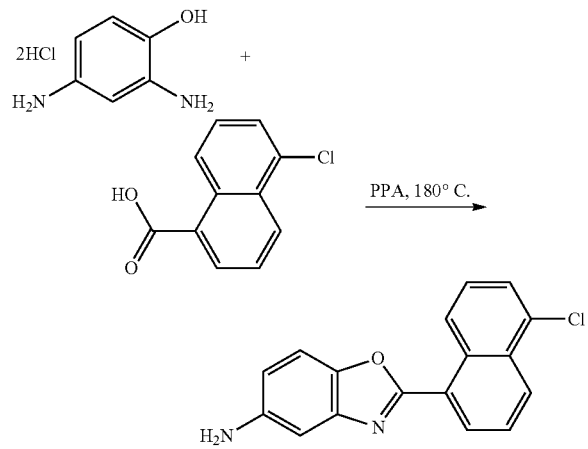

80 μmol of 2,4-diaminophenol.2HCl and 80 μmol of 5-chloro-naphthalene-1-carboxylic acid were dissolved in 100 mg of PPA, and then, the mixed solution was stirred at a temperature of 180° C. for 3 to 4 hours. After completion of the reaction, the reaction solution was cooled, neutralized with 10% NaOH, and filtered by using distilled water for recrystallization in a slow manner, thereby obtaining 18.7 mg of 2-(5-chloronaphthalene-1-yl)benzo[d]oxazole-5-amine (Derivative #5) (yield: 79%).

1H NMR (400 MHz, Chloroform-d) δ 8.45 (dd, J=7.4, 1.5 Hz, 1H), 8.23 (dd, J=6.5, 2.6 Hz, 1H), 8.08 (t, J=7.5 Hz, 1H), 7.92 (dd, J=7.6, 1.5 Hz, 1H), 7.77-7.67 (m, 2H), 7.32 (d, J=1.6 Hz, 1H), 7.22 (d, J=7.4 Hz, 1H), 6.85 (dd, J=7.5, 1.5 Hz, 1H), 4.83 (s, 2H).

Synthesis Example 5

Synthesis of 2-([1,1'-biphenyl]-4-yl)benzo[d]oxazole-5-amine (Derivative #6)

2-([1,1'-biphenyl]-4-yl)benzo[d]oxazole-5-amine (Derivative #6) was synthesized according to Reaction Scheme 5 below:

[Reaction Scheme 5]

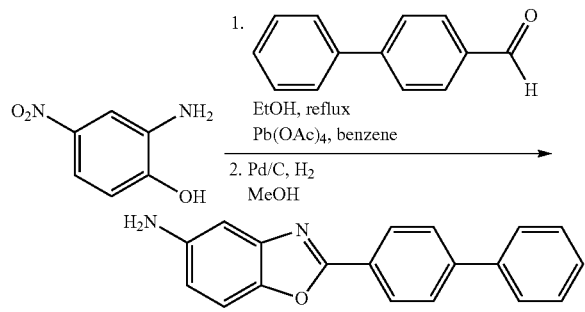

An imine compound, which is a light brown solid, was obtained by refluxing and concentrating 40 mmol of 2-amino-4-nitrophenol and 45 mmol of benzaldehyde, and then, 35 mmol of lead tetraacetate and 100 ml of benzene were added thereto. Then, the mixed solution was stirred at room temperature for 30 minutes. Afterwards, the stirred mixed solution was filtered and concentrated, thereby obtain a nitro compound as an intermediate. The intermediate was dissolved in a methanol solvent, and 5% palladium/activated carbon (Pd/C) (at a weight ratio of 5%) was added thereto, and then, the mixed solution was stirred at room temperature for 2 hours under 1 atmosphere of hydrogen.

Then, the stirred mixed solution was cooled to room temperature, filtered and concentrated, and purified by using silica gel column chromatography (100% chloroform), to obtain a light brown solid product, 2-([1,1'-biphenyl]-4-yl) benzo[d]oxazole-5-amine (Derivative #6) (yield: 53%).

1H NMR (400 MHz, Chloroform-d) δ 8.29 (dd, 2H), 8.27 (dd, 2H), 7.75 (dd, 2H), 7.65-7.45 (m, 2H), 7.42-7.37 (m, 2H), 7.06 (bs, 1H), 6.71 (dd, 1H), 3.75 (s, 2H).

Synthesis Example 6

Synthesis of 2-(3',4',5'-trimethoxy-[1,1'-biphenyl]-4-yl)benzo[d]oxazole-5-amine (Derivative #7)

2-(4-iodinephenyl)-5-nitrobenzo[d]oxazole (Intermediate 1) was synthesized according to Reaction Scheme 6 below:

[Reaction Scheme 6]

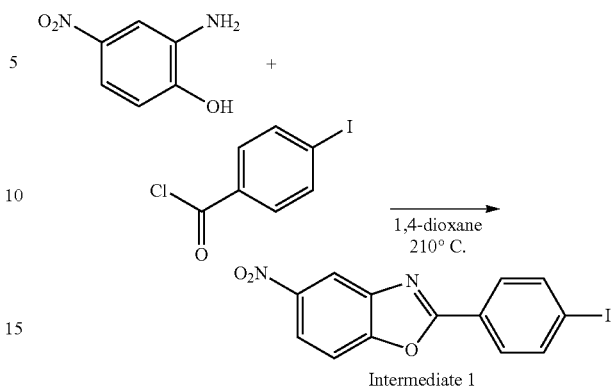

100 mg (0.649 mmol) of 2-amino-4-nitrophenol and 190 mg (0.713 mmol) of 4-iodinebenzoyl chloride were dissolved in 2 mL of a 1,4-dioxane solvent, and then, the mixed solution was subjected to ultrasonication at a temperature of 210° C. for 20 minutes and cooled to a temperature of 55° C. Afterwards, the reaction solution was slowly stirred in 1N NaOH solvent, and then, an organic layer was extracted therefrom by using ethyl acetate to separate an aqueous layer. The organic layer was filtered by using magnesium sulfate (MgSO$_4$), and then, was concentrated and subjected to a silica gel column chromatography (ethyl acetate/n-hexane at a ratio of 1:5) to obtain 53.2 mg of 2-(4-iodinephenyl)-5-nitrobenzo[d]oxazole (Intermediate 1) (yield: 22%).

1H-NMR (600 MHz, Chloroform-d) δ 8.65 (d, J=2.4 Hz, 1H), 8.35 (dd, J=9.0 and 2.4 Hz 1H), 7.99 (m, 2H), 7.94 (m, 2H), 7.69 (d, J=9 Hz, 1H).

Next, 5-nitro-2-(3',4',5'-trimethoxy-[1,1'-biphenyl]-4-yl) benzo[d]oxazole (Intermediate 2) was synthesized according to Reaction Scheme 7 below:

[Reaction Scheme 7]

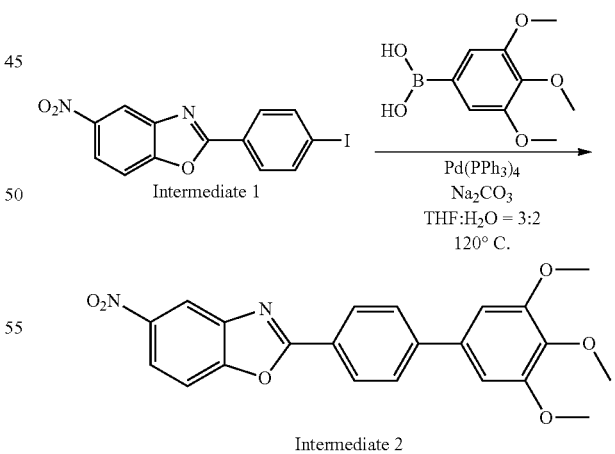

35 mg of 2-(4-iodinephenyl)-5-nitrobenzo[d]oxazole (0.095 mmol) and 25 mg of 3,4,5-trimethoxyphenylboronic acid (0.118 mmol) were dissolved in THF/H$_2$O (at a volume ratio of 12 mL/8 mL) solvent, and then, the mixed solution was heated and refluxed with 40 mg of Na$_2$CO$_3$ (0.377 mmol) and 10 mg of Pd(PPh$_3$)$_4$ (9 mol %) under argon atmophsere. Afterwards, the reaction solution was cooled, and then, an organic layer was extracted therefrom by using ethyl acetate. The organic layer was dried by using magnesium sulfate (MgSO$_4$), and then, was subjected to a silica gel column chromatography (ethyl acetate/n-hexane at a volume ratio of 1:5) to obtain 22 mg (yield=75%) of 5-nitro-2-(3', 4',5'-trimethoxy-[1,1'-biphenyl]-4-yl)benzo[d]oxazole (Intermediate 2).

Next, 2-(3',4',5'-trimethoxy-[1,1'-biphenyl]-4-yl)benzo[d]oxazole-5-amine (Derivative #7) was synthesized according to Reaction Scheme 8 below:

[Reaction Scheme 8]

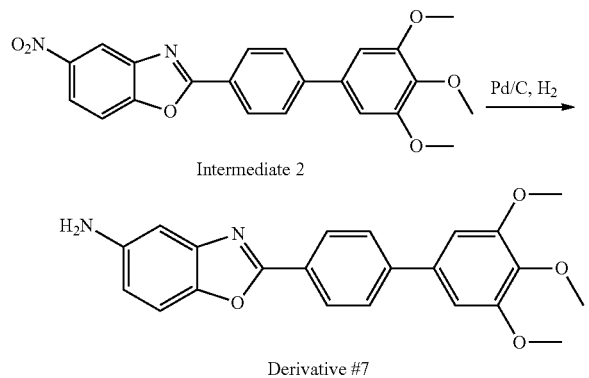

Intermediate 2

Derivative #7

22 mg (0.0541 mmol) of 5-nitro-2-(3',4',5'-trimethoxy-[1,1'-biphenyl]-4-yl)benzo[d]oxazol e was dissolved in methanol, and then, 10% Pd/C was added thereto under hydrogen gas atmosphere. The mixed solution was stirred for 4 hours, and ethyl acetate was added thereto to filter with a celite pad. The filtered solution was concentrated under reduced pressure. Afterwards, the reaction solution was subjected to a silica gel column chromatography (ethyl acetate/normal-hexane at a volume ratio of 1:1) to obtain 15.2 mg (yield=74.6%) of 2-(3',4',5'-trimethoxy-[1,1'-biphenyl]-4-yl)benzo[d]oxazole-5-amine (Derivative #7).

1H-NMR (600 MHz, Chloroform-d) δ 8.26 (d, J=8.4 Hz, 2H), 7.70 (d, J=8.4 Hz, 2H), 7.37 (d, J=8.4 Hz, 1H), 7.07 (d, J=1.8 Hz, 1H), 6.84 (s, 1H), 6.74 (dd, J=9 and 2.4 Hz, 1H), 3.95 (s, 6H), 3.90 (s, 3H); 13C-NMR (150 MHz, Chloroform-d) δ 163.2, 153.6, 144.9, 144.0, 143.6, 143.2, 138.2, 135.9, 127.9, 127.4, 126.1, 113.9, 110.6, 105.1, 104.4, 61.0, 56.2.

Synthesis Example 7

Synthesis of 2-(4'-trifluoromethyl-[1,1'-biphenyl]-4-yl)benzo[d]oxazole-5-amine (Derivative #8)

5-nitro-2-(4'-trifluoromethyl-[1,1'-biphenyl]-4-yl)benzo[d]oxazole (Intermediate 3) was synthesized according to Reaction Scheme 9 below:

[Reaction Scheme 9]

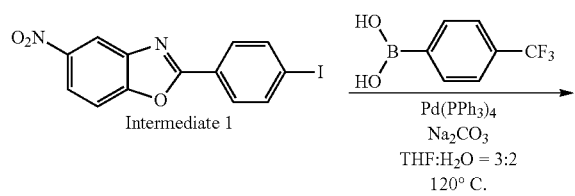

Intermediate 1

Pd(PPh$_3$)$_4$
Na$_2$CO$_3$
THF:H$_2$O = 3:2
120° C.

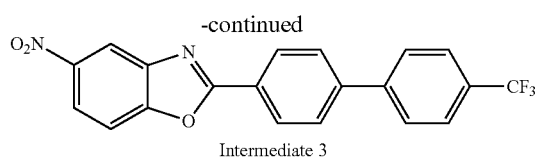

Intermediate 3

A mixture of 35 mg (0.0956 mmol) of 2-(4-iodinephenyl)-5-nitrobenzo[d]oxazole with 22 mg (0.116 mmol) of (trifluoromethyl)phenylboronic acid was added to a THF/H$_2$O (at at volume ratio of 12 mL/8 mL) solution in which 40 mg (0.377 mmol) of Na$_2$CO$_3$ and 10 mg (9 mol %) of Pd(PPh$_3$)$_4$ are dissolved, and then, the mixed solution was heated under argon atmosphere and allowed to react overnight. Afterwards, the reaction solution was refluxed and cooled, and then, an organic layer was extracted therefrom by using ethyl acetate. The organic layer was dried by using magnesium sulfate (MgSO$_4$), and purified by using a silica gel column chromatography (ethyl acetate/normal-hexane at a volume ratio of 1:5) to obtain 27.4 mg (74.6%) of 5-nitro-2-(4'-trifluoromethyl-[1,1'-biphenyl]-4-yl)benzo[d]oxazole (Intermediate 3).

Next, 2-(4'-trifluoromethyl-[1,1'-biphenyl]-4-yl)benzo[d]oxazole-5-amine (Derivative #8) was synthesized according to Reaction Scheme 10 below:

[Reaction Scheme 10]

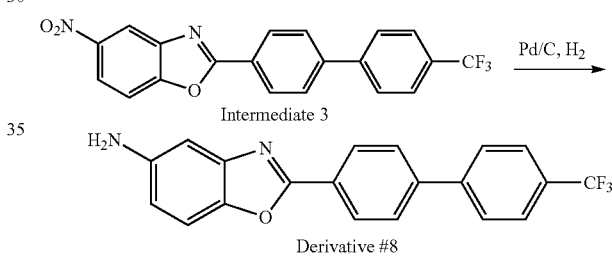

Intermediate 3

Derivative #8

27 mg (0.0703 mmol) of 5-nitro-2-(4'-trifluoromethyl-[1,1'-biphenyl]-4-yl)benzo[d]oxazole was dissolved in methanol, and then, 10% Pd/C was added thereto to allow a catalytic reaction therebetween for 4 hours under hydrogen gas atmosphere. The reaction solution was diluted with ethyl acetate. Then, the diluted reaction solution was filtered with a celite pad, and then, was concentrated under reduced pressure. Afterwards, the filtered reaction solution was purified by using a silica gel column chromatography (ethyl acetate/normal-hexane at a volume ratio of 1:1) to obtain 13.6 mg (54.6%) of 2-(4'-trifluoromethyl-[1,1'-biphenyl]-4-yl)benzo[d]oxazole-5-amine (Derivative #8).

1H-NMR (600 MHz, Chloroform-d) δ 8.36 (d, J=6.6 Hz, 1H), 8.31 (d, J=8.4 Hz, 1H), 7.79 (m, 6H), 7.42 (d, J=8.4 Hz, 1H), 7.09 (s, 1H), 6.80 (d, J=8.4 Hz, 1H).

Synthesis Example 8

Synthesis of 2-(4'-chloro-[1,1'-biphenyl]-4-yl)benzo[d]oxazole-6-ol (Derivative #9)

2-(4-iodinephenyl)-6-methoxybenzo[d]oxazole (Intermediate 4) was synthesized according to Reaction Scheme 11 below:

[Reaction Scheme 11]

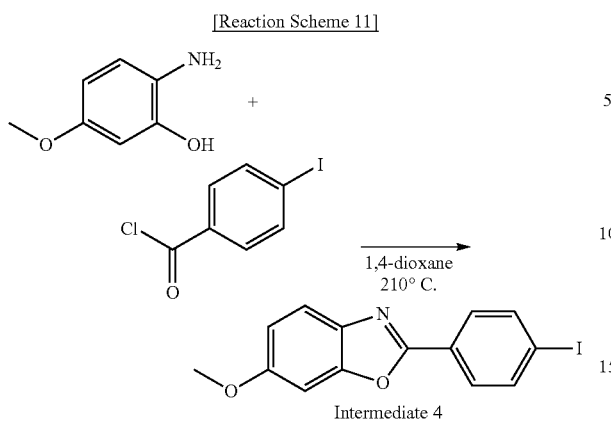

Intermediate 4

100 mg (0.719 mmol) of 2-hydroxy-4-methoxyanilin HCl and 190 mg (0.826 mmol) of 4-iodinebenzoylchlorine were dissolved in 2 ml of a 1,4-dioxane solvent, and then, the mixed solution was subjected to ultrasonication at a temperature of 210° C. for 20 minutes and cooled to a temperature of 55° C. Afterwards, the reaction solution was slowly stirred in 1N NaOH solvent, and then, an organic layer was extracted therefrom by using ethyl acetate to separate an aqueous layer. The organic layer was dried by using magnesium sulfate (MgSO$_4$), and then, was concentrated and subjected to a silica gel column chromatography to obtain 50 mg (yield=19.8%) of 2-(4-iodinephenyl)-6-methoxybenzo[d]oxazole (Intermediate 4).

1H-NMR (600 MHz, Chloroform-d) δ 7.91 (d, J=8.4 Hz, 2H), 7.85 (d, J=8.4 Hz, 2H), 7.63 (d, J=8.4 Hz, 1H), 7.09 (d, J=2.4 Hz, 1H), 6.96 (dd, J=8.4 and 2.4 Hz, 1H), 3.87 (s, 3H); 13C-NMR (150 MHz, Chloroform-d) δ161.4, 158.5, 151.6, 138.1, 135.7, 128.5, 126.8, 120.1, 97.7, 95.4, 55.9.

Next, 2-(4-iodinephenyl)benzo[d]oxazole-6-ol (Intermediate 5) was synthesized according to Reaction Scheme 12 below:

[Reaction Scheme 12]

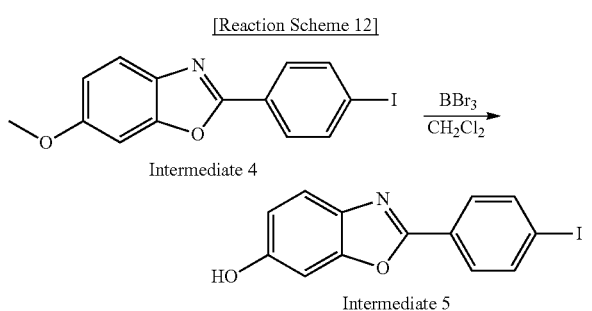

Intermediate 5

50 mg (0.142 mmol) of 2-(4-iodinephenyl)-6-methoxybenzo[d]oxazole and 10% Pd/C were mixed in a MC solution under hydrogen gas atmosphere. Then, a BBr3 MC solution (0.427 mmol 3 eq) was slowly added to the mixed solution at a temperature of −78° C. for 15 minutes, and then, the mixed solution was stirred at room temperature overnight. The reaction mixture was then stabilized with methanol, and was purified by using a silica gel column chromatography (methanol/MC at a volume ratio of 1:20) to obtain 48 mg (100%) of 2-(4-iodinephenyl)benzo[d]oxazole-6-ol (Intermediate 5).

1H-NMR (600 MHz, Chloroform-d) δ 8.10 (s, 1H), 7.92 (d, J=8.4 Hz, 2H), 7.86 (d, J=7.2 Hz, 2H), 7.60 (d, J=8.4 Hz, 1H), 7.06 (d, J=2.4 Hz, 1H), 6.87 (dd, J=8.4 and 2.4 Hz, 1H).

2-(4'-(chloride-[1,1'-biphenyl]-4-yl])benzo[d]oxazole-6-ol (Derivative #9) was synthesized according to Reaction Scheme 13 below:

[Reaction Scheme 13]

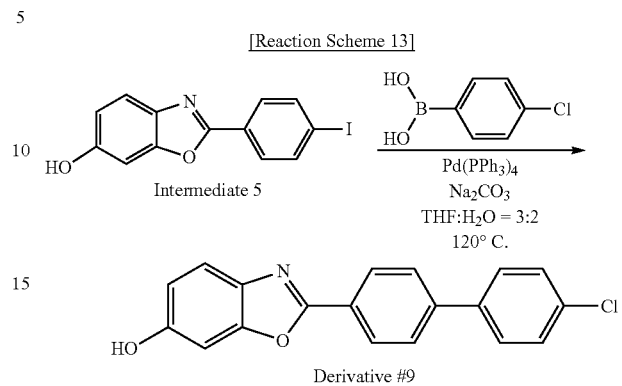

Derivative #9

A mixture of 35 mg (0.104 mmol) of 2-(4-iodinephenyl)-5-benzo[d]oxazole-6-ol with 20 mg (0.128 mmol) of 4-chloridephenylboronic acid were added to a THF/H$_2$O (at at volume ratio of 12 mL/8 mL) solution in which 33 mg (0.311 mmol) of Na$_2$CO$_3$ and 10 mg (8 mol %) of Pd(PPh$_3$)$_4$ are dissolved, and then, the mixed solution was heated under argon atmosphere and allowed to react overnight. Afterwards, the reaction solution was refluxed and cooled, and then, an organic layer was extracted therefrom by using ethyl acetate. The organic layer was dried by using magnesium sulfate (MgSO$_4$), and purified by using silica gel column chromatography (ethyl acetate/normal-hexane at a volume ratio of 1:5) to obtain 21.6 mg (yield=64.7%) of 2-(4'-(chloride-biphenyl-4-yl)benzo[d]oxazole-5-ol (Derivative #9).

1H-NMR (600 MHz, CD$_3$OD) δ 8.23 (d, J=9 Hz, 2H), 7.82 (d, J=7.2 Hz, 2H), 7.70 (d, J=6.6 Hz, 2H), 7.53 (d, J=8.4 Hz, 1H), 7.48 (d, J=8.4 Hz, 2H), 7.06 (d, J=2.4 Hz, 1H), 6.89 (dd, J=8.4 and 1.8 Hz, 1H).

Synthesis Example 9

Synthesis of 2-(2'-methoxy-[1,1'-biphenyl]-4-yl)benzo[d]oxazole-6-ol (Derivative #9)

2-(2'-methoxy-[1,1'-biphenyl]-4-yl)benzo[d]oxazole-6-ol (Derivative #10) was synthesized according to Reaction Scheme 14 below:

[Reaction Scheme 14]

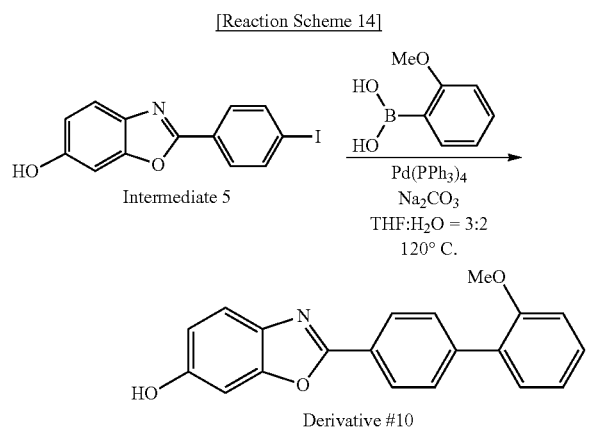

Derivative #10

A mixture of 35 mg (0.104 mmol) of 2-(4-iodinephenyl)-5-benzo[d]oxazole-6-ol with 18 mg (0.118 mmol) of 2-methoxyphenylboronic acid was added to a THF/H$_2$O (at at volume ratio of 12 mL/8 mL) solution in which 33 mg (0.311 mmol) of Na$_2$CO$_3$ and 10 mg (8 mol %) of Pd(PPh$_3$)$_4$ are dissolved, and then, the mixed solution was heated under argon atmosphere and allowed to react overnight. Afterwards, the reaction solution was refluxed and cooled, and then, an organic layer was extracted therefrom by using ethyl acetate. The organic layer was dried by using magnesium sulfate (MgSO$_4$), and purified by using a silica gel column chromatography (ethyl acetate/normal-hexane at a volume ratio of 1:5) to obtain 15.8 mg (yield=48%) of 2-(2'-methoxy-[1,1'-biphenyl]-4-yl)benzo[d]oxazole-6-ol (Derivative #10).

1H-NMR (600 MHz, CDCl$_3$) δ 8.23 (d, J=6 Hz, 2H), 7.69 (d, J=6 Hz, 2H), 7.61 (d, J=9 Hz, 1H), 7.37 (t, J=8.4 Hz 2H), 7.09 (s, 1H), 7.07 (t, J=6.9 Hz 1H), 7.02 (d, J=7.8 Hz 1H), 6.88 (dd, J=8.4 and 2.4 Hz, 1H), 5.71 (s, 1H), 3.84 (s, 3H); 13C-NMR (150 MHz, CDCl$_3$) δ162.5, 156.5, 154.1, 151.5, 141.6, 136.0, 130.7, 130.0, 129.6, 129.3, 126.9, 125.5, 120.9, 119.9, 113.2, 111.3, 97.8, 55.6.

Example 1

Observation of Nrf2 Inhibitor

1. Cell Culture, Cell Transformation, and Luciferase Analysis

Lung cancer cells (H1299) purchased from American Type Culture Collection (ATCC, CRL-5803™) were cultured in Dulbecco's modified Eagle's medium (DMEM) enriched with 10% fetal bovine serum (FBS), 100 μg/ml of streptomycin, and 100 unit/ml of penicillin, under conditions of 5% CO$_2$ and a temperature of 37° C.

Then, the cells were transformed by using Lipofectamine 2000 (In vitrogen, Life technologies, USA) (i.e., a plasmid transfection reagent used in DMEM) so that an antioxidant response element (ARE)-pGL3 luciferase plasmid to which an Nrf2 transcription factor can bind was introduced to the cells, according to the manufacturer's instructions.

About 20,000 of the transformed cells were inoculated in each well of a 96-well plate, and then, the cells were cultured for 24 hours under the same conditions described above. Afterwards, tertiary butylhydroquinone (tBHQ) that activates ARE was added to each well. Accordingly, it was confirmed that activity of luciferase was increased at least about 3 times as large as activity of luciferase in cells that were not treated with tBHQ.

Next, the tBHQ-treated cells were additionally treated with 2-(5-bromonaphthalene-1-yl)benzo[d]oxazole-5-amine (ChemBridge, cat#5721754, San Diego, Calif., USA) (Derivative #1) in concentration of 1 μM, 5 μM, and 10 μM, and then, were incubated for 18 hours. Accordingly, activity of luciferase was confirmed by using a Victor 3 luminometer (Perkin Elmer, USA) and a luciferase analysis kit (Promega, Medison, Wis., USA).

As a result, as shown in FIG. 1, it was confirmed that the inhibitory activity of ARE-responsive luciferase was dependent upon concentration of 2-(5-bromonaphthalene-1-yl)benzo[d]oxazole-5-amine (Derivative #1).

Here, in order to confirm that the inhibitory activity of luciferase was caused by an Nrf2 inhibitor, rather than by apoptosis of the cells, cell counting kit-8 (CCK-8) (Dojindo, Japan) for the determination of cell viability and a spectroscopic device (Labsystems, USA) were used to measure absorbance values of the cells at a wavelength of 480 nm.

Figure 2:
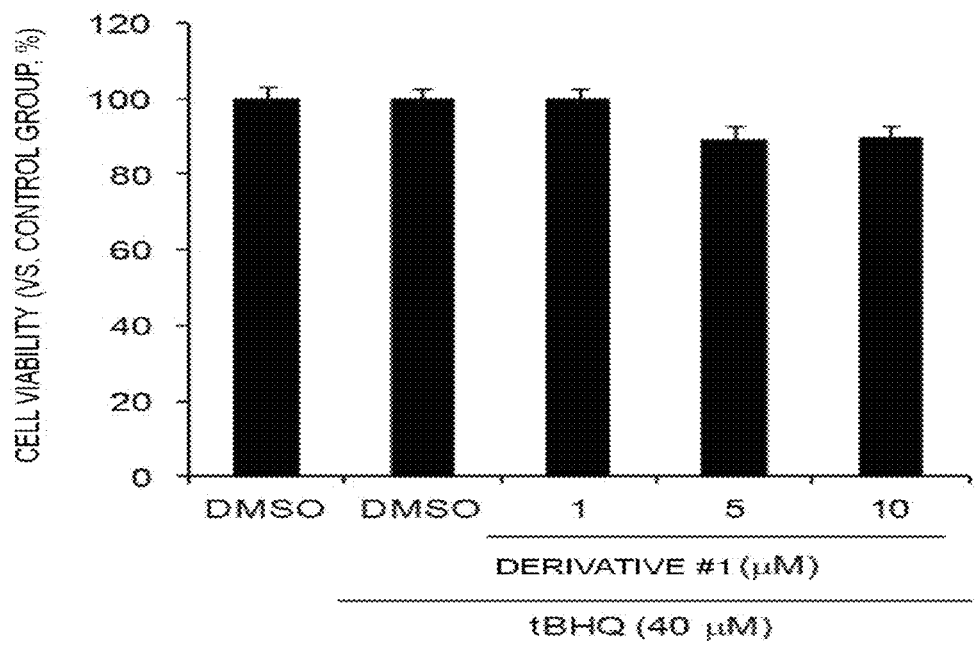
FIG. 2 shows a result of CCK-8 viability analysis in a case where lung cancer cell is treated with an Nrf2 inhibitor, i.e., 2-(5-bromonaphthalene-1-yl)benzo[d]oxazole-5-amine (Derivative #1) in a concentration of 1 μM, 5 μM, and 10 μM, to confirm cytotoxicity of 2-(5-bromonaphthalene-1-yl)benzo[d]oxazole-5-amine (Derivative #1) synthesized according to an embodiment.

As a result, as shown in FIG. 2, it was confirmed that 2-(5-bromonaphthalene-1-yl)benzo[d]oxazole-5-amine (Derivative #1) itself had no cytotoxicity.

Then, in order to confirm whether the benzo[d]oxazole derivatives (Derivatives #2 to #10) of Synthesis Examples 1 to 9 had inhibitory activity of Nrf2, 2-(naphthalene-1-yl) benzo[d]oxazole-5-amine (Derivative #2); 2-(naphthalene-2-yl)benzo[d]oxazole-5-amine (Derivative #3); 2-(4-tert-butylphenyl)benzo[d]oxazole-5-amine (Derivative #4); 2-(5-chloronaphthalene-1-yl)benzo[d]oxazole-5-amine (Derivative #5); 2-([1,1'-biphenyl]-4-yl)benzo[d]oxazole-5-amine (Derivative #6); 2-(3',4',5'-trimethoxy-[1,1'-biphenyl]-4-yl)benzo[d]oxazole-5-amine (Derivative #7); 2-(4'-trifluoromethyl-[1,1'-biphenyl]-4-yl)benzo[d]oxazole-5-amine (Derivative #8); 2-(4'-chloro-[1,1'-biphenyl]-4-yl)benzo[d]oxazole-6-ol (Derivative #9); and 2-(2'-methoxy-[1,1'-biphenyl]-4-yl)benzo[d]oxazole-6-ol (Derivative #10) were used to compare the activity of the ARE-pGL3 luciferase in the lung cancer cells (H1299) that are not transformed with the activity of the ARE-pGL3 luciferase in the lung cancer cells (H1299) that were transformed to allow expression of the ARE-pGL3 luciferase plasmid and to enhance the inhibitory activity of the ARE-pGL3 luciferase.

Figure 3:
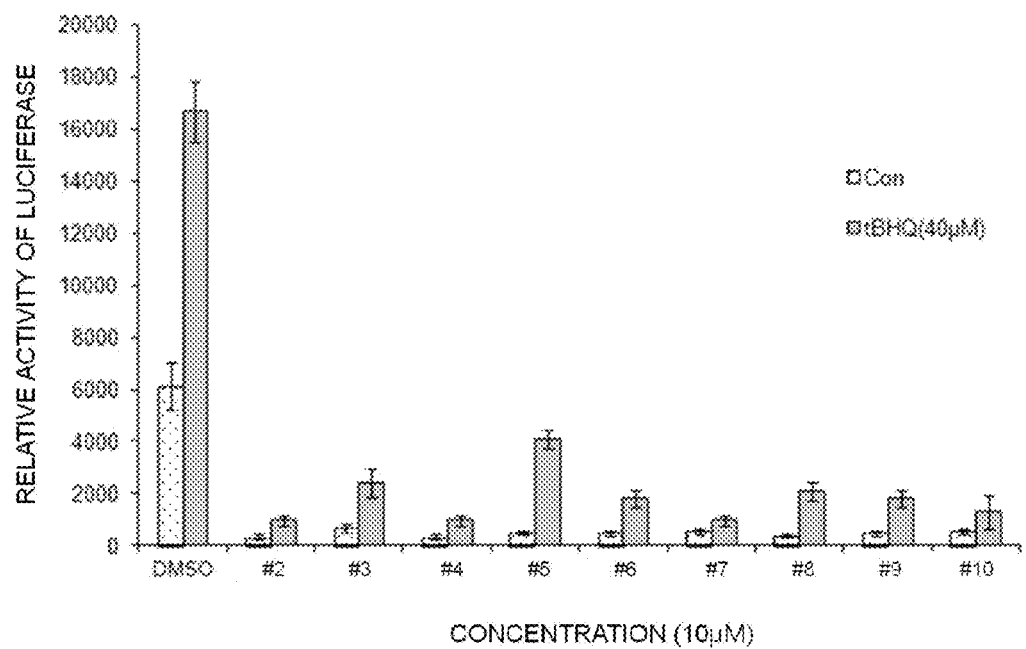
FIG. 3 is a graph comparing inhibitory effects of Nrf2-responsive luciferase induced by tBHQ in an experimental group and those in a control group in which the experimental group is prepared by treating lung cancer cell strain with 10 μM of each of benzo[d]oxazole derivates 2 to 10 and the control group is free from any treatment.

As a result, as shown in FIG. 3, it was confirmed that the cases where the lung cancer cells (H1299) were treated with Derivatives #2 to #10 in a concentration of 10 μM showed inhibitory activity of luciferase, the activity of luciferase being increased by former tBHQ treatment.

Figure 4:
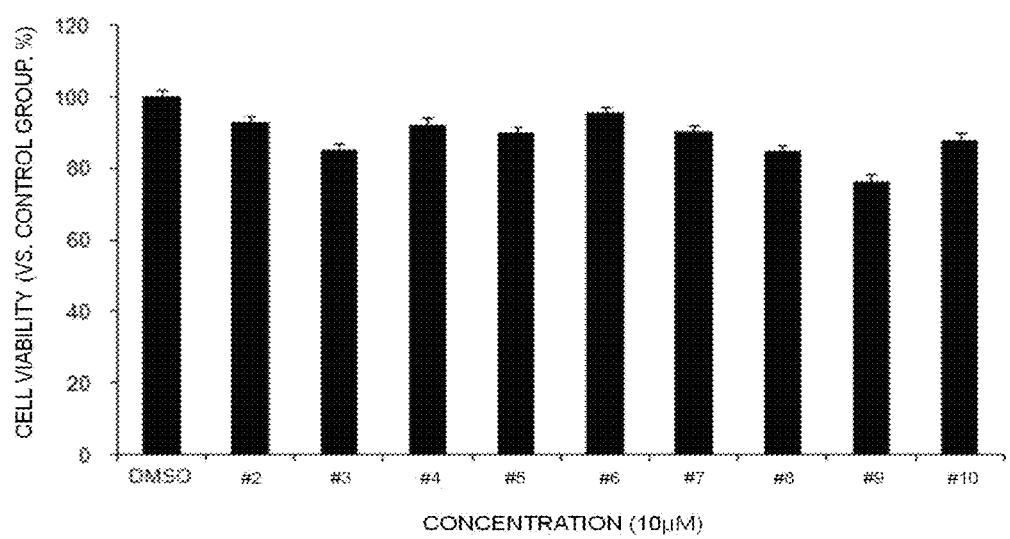
FIG. 4 shows a result of CCK-8 viability analysis in a case where lung cancer cell is treated with 10 μM of each of benzo[d]oxazole derivates (Derivatives #2 to #10) to confirm cytotoxicity of benzo[d]oxazole derivatives (Derivatives #2 to #10) synthesized according to embodiments

Here, in order to confirm that the inhibitory activity of luciferase was caused by Nrf2 inhibitors, i.e., Derivative #2 to #10, rather than by apoptosis of the cells, CCK-8 (Dojindo, Japan) for the determination of cell viability and a spectroscopic device (Labsystems, USA) were used to measure absorbance values of the cells at a wavelength of 480 nm. As a result, as shown in FIG. 4, it was confirmed that the benzo[d]oxazole derivatives (Derivatives #2 to #10) themselves had no cytotoxicity.

Example 2

Target Confirmation of Nrf2 Inhibitor

By using a western blot, it was confirmed whether 2-(5-bromonaphthalene-1-yl)benzo[d]oxazole-5-amine (Derivative #1), which is a Nrf2 inhibitor, has targeted a Nrf2 protein and its downstream antioxidant enzyme heme oxygenase (HO)-1, based on the inhibitory activity of the ARE-pGL3 luciferase.

The lung cancer cells were treated with 2-(5-bromonaphthalene-1-yl)benzo[d]oxazole-5-amine (Derivative #1) in a concentration of about 5 μM or about 10 μM, and 2 hours later, the protein expression was analyzed to measure amounts of Nrf2 and HO-1 proteins, which were increased by tBHQ treatment.

First, the cells treated with 2-(5-bromonaphthalene-1-yl) benzo[d]oxazole-5-amine (Derivative #1) were obtained, and then, cytosolic fractions were obtained therefrom by using a method commonly used in the art.

The cytosolic fractions were separated by electrophoresis using 10% gradient SDS-PAGE, and then, were transferred to a nitrocellulose membrane (BioRad, Hercules, Calif., USA). The membrane was blocked with 5% skim milk, and then, a reaction with primary antibodies, e.g., anti-Nrf2 (Abcam, USA) and an HO-1 antibody (Oncogene Research Products, USA), was allowed. Afterwards, a reaction with a horseradish peroxidase-conjugated anti-rat IgG antibody (Santa Cruz Biotechnology, USA) was complete at a constant temperature, and the results obtained therefrom were visualized by using an ECL system (GE, USA).

Referring to FIG. 5, the amounts of Nrf2 and HO-1 proteins that were increased by the tBHQ treatment were reduced depending on the concentration of 2-(5-bromonaphthalene-1-yl)benzo[d]oxazole-5-amine (Derivative #1) to be treated.

In this regard, it was confirmed that 2-(5-bromonaphthalene-1-yl)benzo[d]oxazole-5-amine (Derivative #1), i.e., an Nrf2 inhibitor, stimulated ARE to inhibit a binding of the Nrf2 transcription factor thereto, thereby inhibiting the expression of antioxidant enzyme HO-1.

Example 3

Confirmation of Inhibition of ROS Production

The lung cancer cells (H1299) that were cultured in the same manner as in Example 1 were treated with dihydrodichlorofluorescein diacetate (DCF-DA, Sigma, USA) and were subjected to fluorescence staining. The stained cells were then treated with 2-(5-bromonaphthalene-1-yl)benzo[d]oxazole-5-amine (Derivative #1) for 2 hours in a concentration of 5 μM or 10 μM, and 5 Gy of irradiation. Afterwards, an increase in ROS production upon inhibition of Nrf2 was analyzed by FACS.

As a result, as shown in FIGS. 6 and 7, it was confirmed that the ROS production in a case where the lung cancer cells (H1299) were treated in combination with 2-(5-bromonaphthalene-1-yl)benzo[d]oxazole-5-amine (Derivative #1) in a concentration of 5 μM or 10 μM and 5 Gy of irradiation was increased about 3.5 times or 4.6 times as large as the ROS production in a case where the lung cancer cells (H1299) were treated with 5 Gy of irradiation only.

In addition, in order to confirmed whether the values measured by FACS analysis refer to the ROS production, the lung cancer cells (H1299) were treated with 2 mM of N-acetyl-L-cysteine (NAC), which is a ROS inhibitor, and then, were treated in combination with 2-(5-bromonaphthalene-1-yl)benzo[d]oxazole-5-amine (Derivative #1) in a concentration of 10 μM and irradiation. As a result, it was confirmed that the ROS production was inhibited.

Example 4

Effects on Cell Apoptosis by Treatment Using Nrf2 Inhibitor and Anticancer Agent in Combination or Nrf2 Inhibitor and Radiation in Combination 1. Apoptotic Effects on Cancer Cells According to Treatment Using an Nrf2 Inhibitor in Combination with an Anticancer Agent or Radiation Lung cancer cells (H1299, ATCC, CRL-5803™), brain cancer cells (U87MG, ATCC, HTB-14™ human glioblastoma), breast cancer cells (MDA-MB231, ATCC, HTB-26™ human breast adenocarcinoma), and colorectal cancer cells (HCT116, ATCC, CCL-247™ human colorectal carcinoma) were each inoculated in each well of a 96-well plate containing Rosewell Park Memorial Institute medium (RPMI) 1640 enriched with 10% FBS, 100 μg/ml of streptomycin, and 100 unit/ml of penicillin. Then, these cells were each treated with 2-(5-bromonaphthalene-1-yl)benzo[d]oxazole-5-amine (Derivative #1) for 2 hours in a concentration of 1 μM to 10 μM, were irradiated using gamma radiation according to radiation dose, and were cultured for 7 days under conditions of 5% $CO_2$ and a temperature of 37° C. The cultured cells were washed out with phosphate buffered saline (PBS), and then, were stained with a mixture of 1% methylene blue and 100% methanol. Afterwards, a number of colony-forming cells was counted, and all the treatment above were repeatedly performed 3 times.

As a result, as shown in FIGS. 8 to 11, it was confirmed that the treatment with 2-(5-bromonaphthalene-1-yl)benzo[d]oxazole-5-amine (Derivative #1) increased apoptotic effects on the cancer cells by irradiation. Accordingly, it was also confirmed that 2-(5-bromonaphthalene-1-yl)benzo[d]oxazole-5-amine (Derivative #1) can be used as a sensitizer to enhance the apoptotic effects on the cancer cells during radiation therapy.

In addition, the lung cancer cell strain (H1299) was treated with each of the synthesized benzo[d]oxazole derivatives (Derivatives #2 to #10) in a concentration of 10 μM, and then, was treated with 5 Gy of irradiation. After 48 hours of the treatment, CCK-8 for the determination of cell viability was used to measure cytotoxicity of the lung cancer cells.

As a result, as shown in FIG. 12, it was confirmed that the cancer cells in experimental groups treated with only irradiation showed capability of cancer cell apoptosis that was increased by 20% as compared with capability of the cancer cells in a control group without treatment. It was also confirmed that the cancer cells in experimental groups treated in combination with the benzo[d]oxazole derivatives showed capability of cancer cell apoptosis that was increased about 1.7 to about 3.5 times as large as capability of the cancer cells in a control group.

Accordingly, it was confirmed that the cases where the cancer cells were treated in combination with the synthesized benzo[d]oxazole derivatives (Derivatives #2 to #10) and irradiation may increase sensitivity of the cancer cells to radiation, so that the synthesized benzo[d]oxazole derivatives can be used as a radiosensitive enhance during radiation therapy.

2. Therapeutic Effects of Treatment in Combination with an Anticancer Agent

In order to confirm whether the above-described benzo[d]oxazole derivative that increases the apoptotic effects of ROS also have such apoptotic effects when the benzo[d]oxazole derivative is used in combination with, other than radiation, an anticancer agent to produce ROS, the synthesized benzo[d]oxazole derivative was treated in combination with doxorubicin, which is an anticancer agent.

The lung cancer cell strain (H1299) was treated with each of the synthesized benzo[d]oxazole derivatives (Derivatives #1 to #10) for 2 hours in a concentration of 10 μM, and then, were treated with doxorubicin in a concentration of 150 nM. After 48 hours of the treatment, CCK-8 for the determination of cell viability was used to measure the lung cancer cells that were died by apoptosis.

Figure 13:
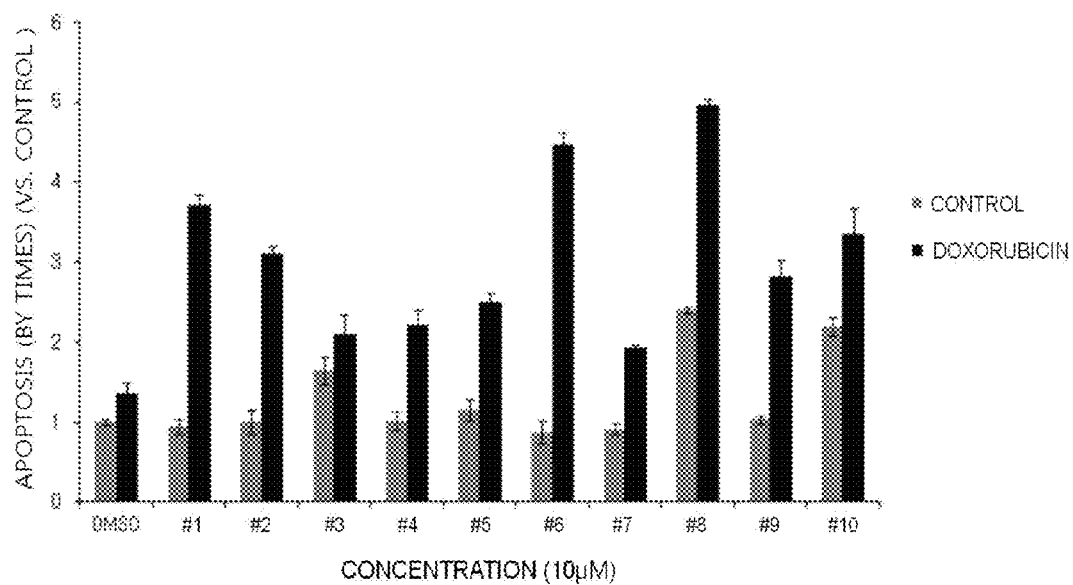
FIG. 13 shows a result of anticancer agent sensitivity based on a number of apoptosis measured after cells of lung cancer cell strain (H1299) are treated with 10 μM of each of benzo[d]oxazole derivatives (Derivates 2 to 10) and doxorubicin in combination.

As a result, as shown in FIG. 13, it was confirmed that the cancer cells in experimental groups treated with only doxorubicin had apoptotic cell death that is increased about 1.35 times as large as apoptotic cell death of the cancer cells in a control group. However, the cancer cells in experimental group treated with 2-(5-bromonaphthalene-1-yl)benzo[d]oxazole-5-amine (Derivative #1) had apoptotic cell death that is increased about 3.7 times as large as apoptotic cell death of the cancer cells in a control group while the cancer cells in experimental group treated with other derivatives had apoptotic cell death that is increased about 2.1 to about 4.5 times as large as apoptotic cell death of the cancer cells in a control group.

Accordingly, it was confirmed that the synthesized benzo[d]oxazole derivatives are capable of increasing sensitivity of a cancer cell to an anticancer agent.

As described above, according to the one or more of the above exemplary embodiments, unlike the case where cancer cells of lung cancer, brain cancer, breast cancer, or colorectal cancer are treated only with radiation, the case where cancer cells are treated in combination with a composition containing a benzo[d]oxazole derivative are capable of increasing apoptotic effects on these cancer cells. In addition, when the composition containing the synthesized benzo[d]oxazole derivative is administered in combination with doxorubicin, which is as an anticancer agent, to the cancer cells of lung cancer, enhanced anticancer therapeutic effects are shown compared to the case where the cancer cells are treated only with doxorubicin. Therefore, the composition containing the synthesized benzo[d]oxazole derivative can be used as an anticancer supplement agent, and is capable of increasing anticancer therapeutic effects in combined treatment with radiation or in combined administration with an anticancer agent.

It should be understood that the exemplary embodiments described therein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

What is claimed is:

1. An anticancer supplement agent comprising a benzo[d]oxazole compound as an effective ingredient that is represented by the following Formula:

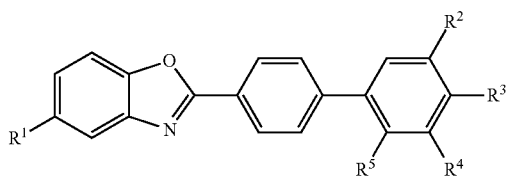

wherein
R$^1$ is —NH, or —OH,
each of R$^2$ to R$^5$ is identical or different, and is selected from the hydrogen, a C$_1$ alkoxy group, trifluoromethyl, and halogen.

2. The anticancer supplement agent of claim 1, wherein the benzo[d]oxazole compound is selected from the group consisting of 2-([1,1'-biphenyl]-4-yl)benzo[d]oxazole-5-amine, 2-(3',4',5'-trimethoxy-[1,1'-biphenyl]-4-yl)benzo[d]oxazole-5-amine, 2-(4'-trifluoromethyl-[1,1'-biphenyl]-4-yl)benzo[d]oxazole-5-amine, 2-(4'-chloro-[1,1'-biphenyl]-4-yl)benzo[d]oxazole-6-ol, and 2-(2'-methoxy-[1,1'-biphenyl]-4-yl)benzo[d]oxazole-6-ol.

3. The anticancer supplement agent of claim 1, wherein the benzo[d]oxazole compound increases apoptotic effects thereof on a cancer cell by inhibiting activity of an Nrf2 gene.

4. The anticancer supplement agent of claim 1, wherein the benzo[d]oxazole compound increases anticancer activity of an anticancer agent used in anticancer agent therapy or radiation used in radiation therapy.

5. The anticancer supplement agent of claim 4, wherein the anticancer agent is selected from the group consisting of a platinum-based anticancer agent, an alkylated anticancer agent, and an anthracycline-based anticancer agent.

6. A method of treating lung cancer, brain cancer, breast cancer or colorectal cancer in a subject in need there of, comprising:

providing a pharmaceutical composition comprising an anticancer agent and a benzo[d]oxazole compound as an effective ingredient that is represented by the following Formula

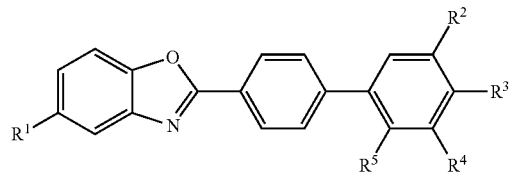

wherein,
R$^1$ is —NH, or —OH,
each of R$^2$ to R$^5$ is identical or different, and is selected from the hydrogen, a C$_1$ alkoxy group, trifluoromethyl, and halogen; and
administering the pharmaceutical composition to the subject, wherein the cancer is treated.

7. The method of claim 6, wherein the benzo[d]oxazole compound is selected from the group consisting of 2-([1,1'-biphenyl]-4-yl)benzo[d]oxazole-5-amine, 2-(3',4',5'-trimethoxy-[1,1'-biphenyl]-4-yl)benzo[d]oxazole-5-amine, 2-(4'-trifluoromethyl-[1,1'-biphenyl]-4-yl)benzo[d]oxazole-5-amine, 2-(4'-chloro-[1,1'-biphenyl]-4-yl)benzo[d]oxazole-6-ol, and 2-(2'-methoxy-[1,1'-biphenyl]-4-yl)benzo[d]oxazole-6-ol.

8. The method of claim 6, wherein anticancer agent is selected from the group consisting of a platinum-based anticancer agent, an alkylated anticancer agent, and an anthracycline-based anticancer agent.

9. A radiosensitive enhancer in radiation therapy, the enhancer comprising a benzo[d]oxazole derivate as an effective ingredient that is represented by the following Formula (a) or (b):

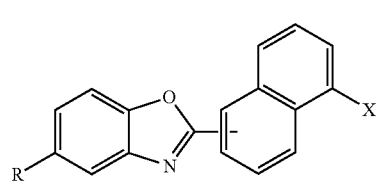

Formula (a)

wherein,
R is —NH$_2$ or —OH,
X is hydrogen or halogen,

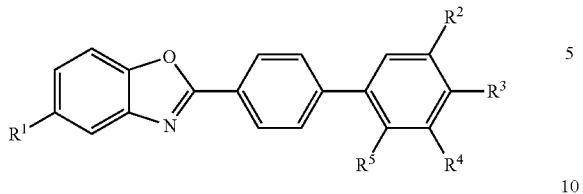

Formula (b)

wherein,

R¹ is —NH, or —OH, each of R² to R⁵ is identical or different, and is selected from the hydrogen, a C₁ alkoxy group, trifluoromethyl, and halogen.

10. The radiosensitive enhancer of claim 9, wherein the benzo[d]oxazole compound is selected from the group consisting of 2-(5-bromonaphthalene-1-yl)benzo[d]oxazole-5-amine, 2-(naphthalene-1-yl)benzo[d]oxazole-5-amine, 2-(naphthalene-2-yl)-benzo[d]oxazole-5-amine, 2-(4-tert-butylphenyl)benzo[d]oxazole-5-amine, 2-(5-chloronaphthalene-1-yl)benzo[d]oxazole-5-amine, 2-([1,1'-biphenyl]-4-yl)benzo[d]oxazole-5-amine, 2-(3',4',5'-trimethoxy-[1,1'-biphenyl]-4-yl)benzo[d]oxazole-5-amine, 2-(4'-trifluoromethyl-[1,1'-biphenyl]-4-yl)benzo[d]oxazole-5-amine, 2-(4'-chloro-[1,1'-biphenyl]-4-yl)benzo[d]oxazole-6-ol, and 2-(2'-methoxy-[1,1'-biphenyl]-4-yl)benzo[d]oxazole-6-ol.

\* \* \* \* \*